(12) United States Patent
Murata et al.

(10) Patent No.: US 7,046,270 B2
(45) Date of Patent: May 16, 2006

(54) STEREOSCOPIC OBSERVATION SYSTEM

(75) Inventors: Masanao Murata, Higashiyamato (JP); Shingo Kato, Sagamihara (JP)

(73) Assignee: Olympus Corporation, Tokyo (JP)

( * ) Notice: Subject to any disclaimer, the term of this patent is extended or adjusted under 35 U.S.C. 154(b) by 652 days.

(21) Appl. No.: 10/177,525

(22) Filed: Jun. 21, 2002

(65) Prior Publication Data

US 2003/0060679 A1    Mar. 27, 2003

(30) Foreign Application Priority Data

Jun. 25, 2001    (JP)    ............................. 2001-191556

(51) Int. Cl.
*A61B 1/04* (2006.01)
*H04N 13/00* (2006.01)
*H04N 15/00* (2006.01)

(52) U.S. Cl. ............................. 348/45; 348/49; 348/52; 348/53

(58) Field of Classification Search .................. 348/45, 348/176, 178; 600/111; 345/8
See application file for complete search history.

(56) References Cited

U.S. PATENT DOCUMENTS

| | | | |
|---|---|---|---|
| 4,709,263 A * | 11/1987 | Brumage | 348/42 |
| 4,873,572 A | 10/1989 | Miyazaki et al. | |
| 5,579,026 A * | 11/1996 | Tabata | 345/8 |
| 5,790,184 A | 8/1998 | Sato et al. | |
| 5,860,912 A * | 1/1999 | Chiba | 600/111 |
| 6,063,023 A | 5/2000 | Sakiyama et al. | |
| 6,108,005 A * | 8/2000 | Starks et al. | 345/419 |
| 6,139,490 A * | 10/2000 | Breidenthal et al. | 600/111 |
| 6,181,304 B1 * | 1/2001 | Robinson et al. | 345/8 |

FOREIGN PATENT DOCUMENTS

| | | | | |
|---|---|---|---|---|
| JP | 63-244011 | 10/1988 | | |
| JP | 09252478 | * 9/1997 | | 13/4 |
| JP | 10-248806 | 9/1998 | | |

* cited by examiner

*Primary Examiner*—Vivek Srivastava
*Assistant Examiner*—Justin Shepard
(74) *Attorney, Agent, or Firm*—Scully, Scott, Murphy & Presser, P.C.

(57) ABSTRACT

A stereoscopic video image is observed by displaying to left and right display devices arranged in front of the left and right eyes of an observer, left and right images formed on an image pick-up device by using a stereoscopic optical system. Then, a read address of image data stored in a memory is changed by operating a display position adjusting pick or the like, thereby simply variably adjusting the display positions of the left and right images. As a consequence, it is possible to respond to the case in which a parallax of the observer is varied.

17 Claims, 18 Drawing Sheets

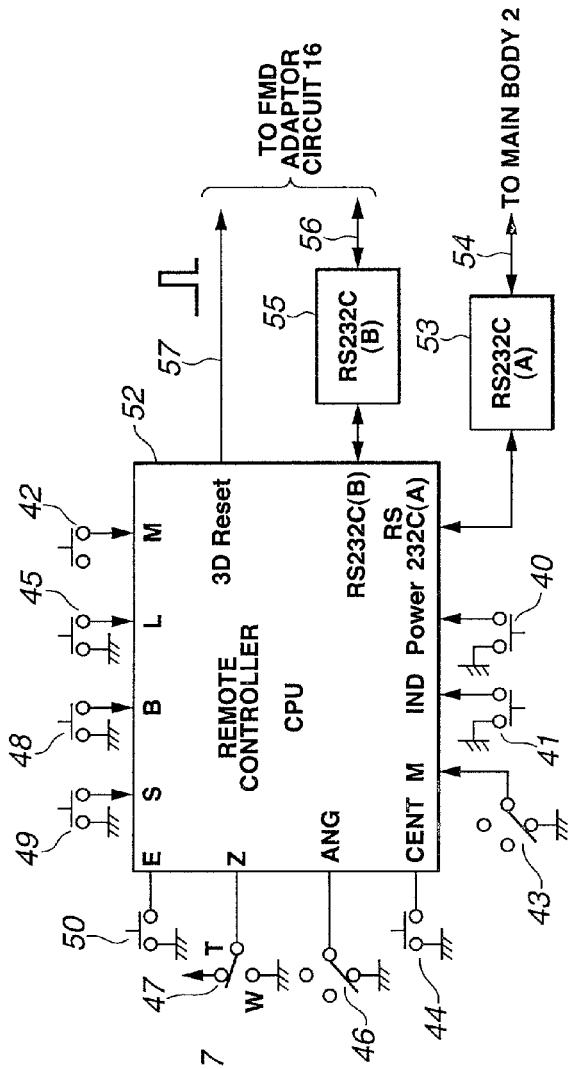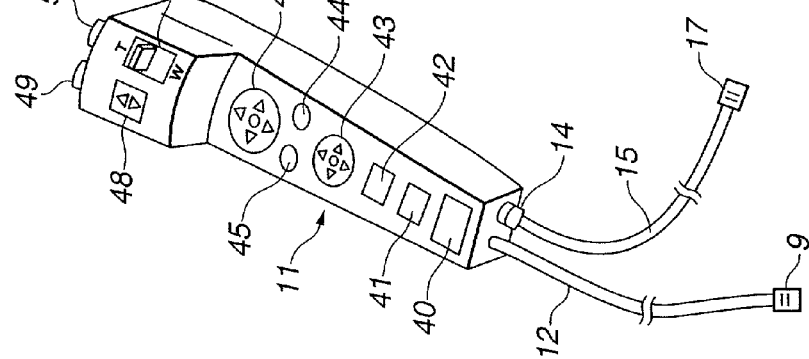

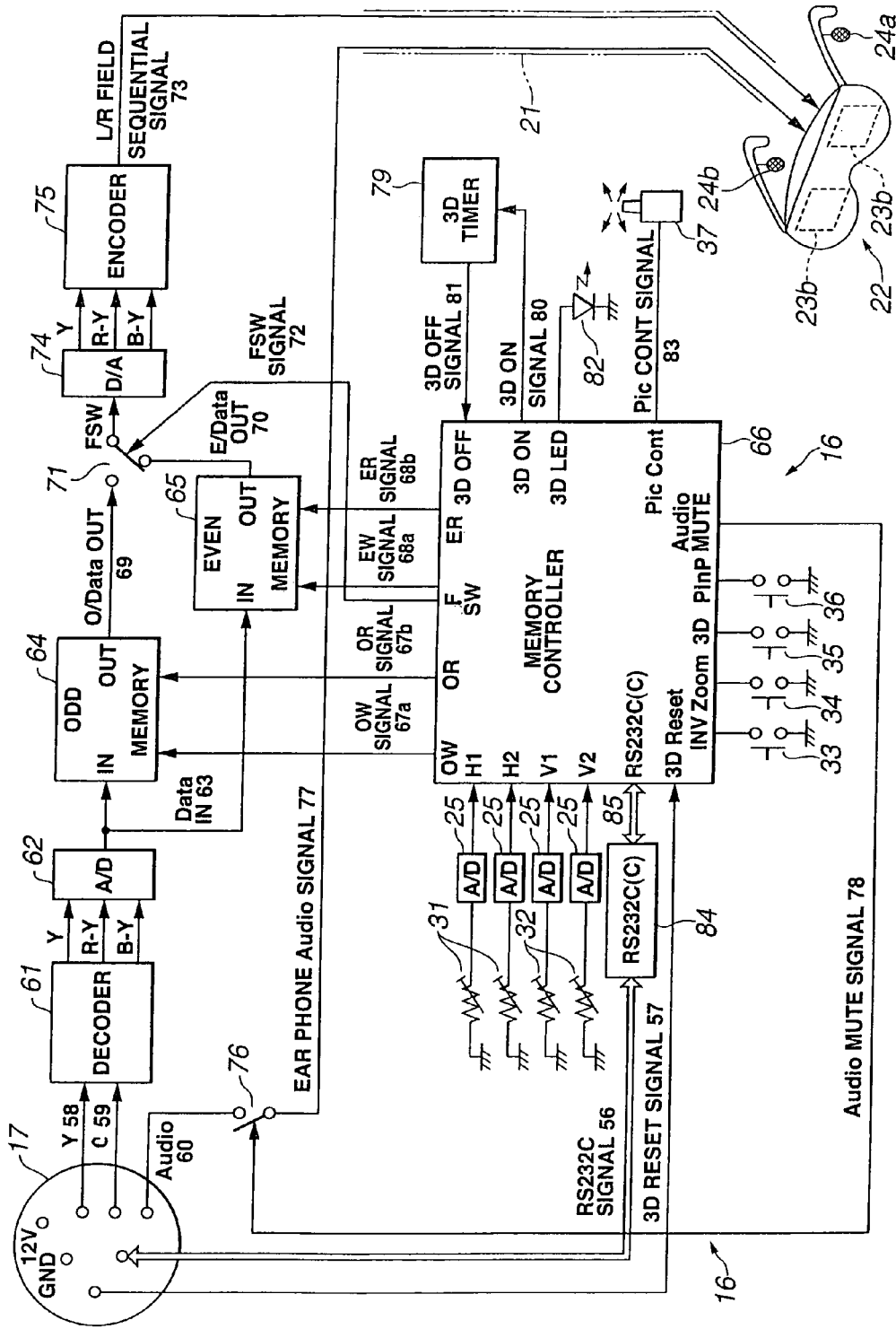

FIG.7A
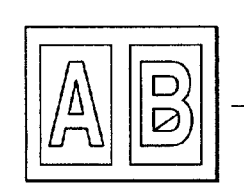
ORIGINAL IMAGE 86
(=Y SIGNAL 58,
C SIGNAL 59)
FIG.7B
LEFT LCD 23a    RIGHT LCD 23b
2D MODE
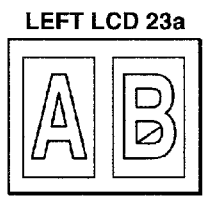 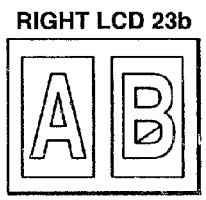
FIG.7C
INV MODE
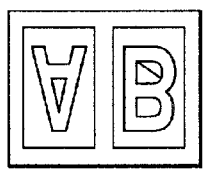 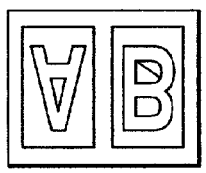
FIG.7D
Zoom MODE
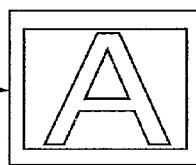 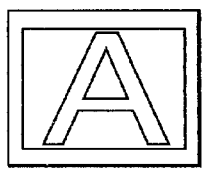
FIG.7E
87  88
P in P MODE
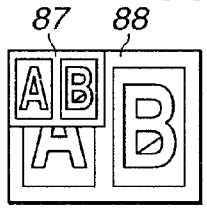 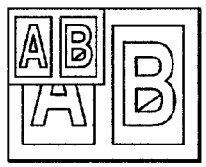
FIG.7F
SHIFT IN HORIZONTAL DIRECTION
3D MODE
(Zoom)
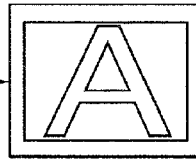 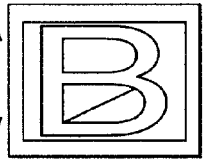
SHIFT IN VERTICAL DIRECTION
FIG.7G
SHIFT IN HORIZONTAL DIRECTION
3D MODE
(NO Zoom)
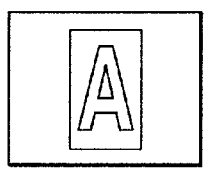 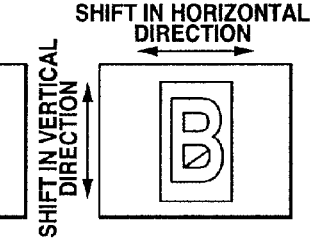
SHIFT IN VERTICAL DIRECTION

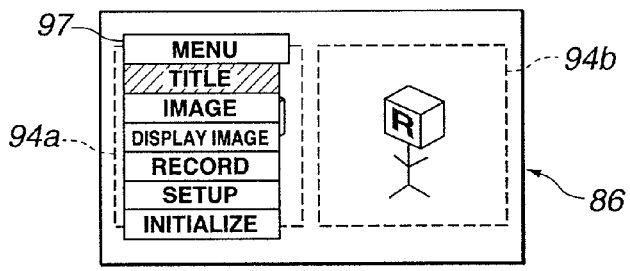
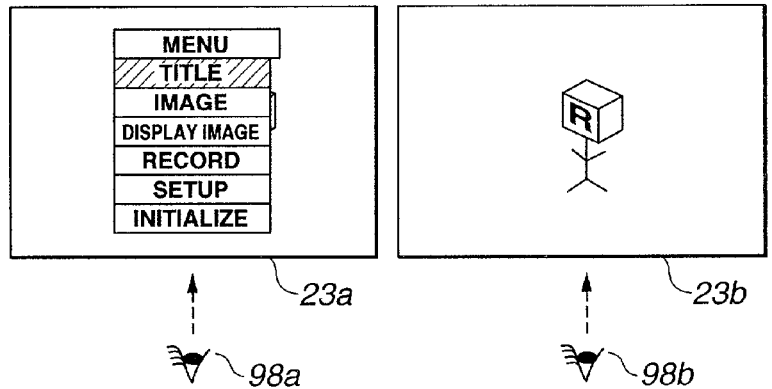
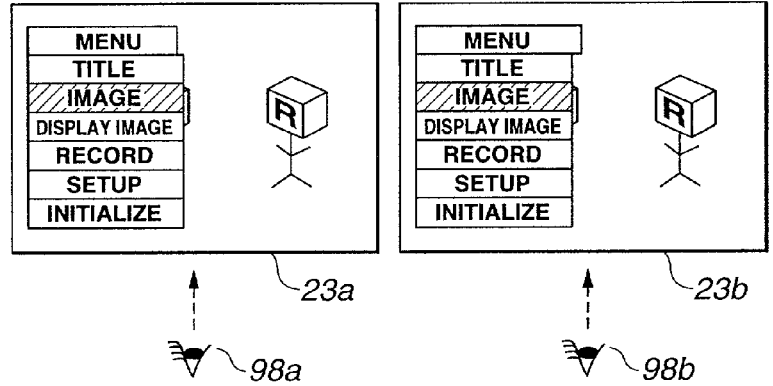

FIG.11A
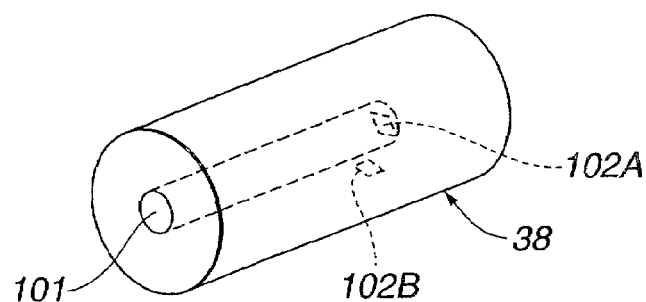
FIG.11B
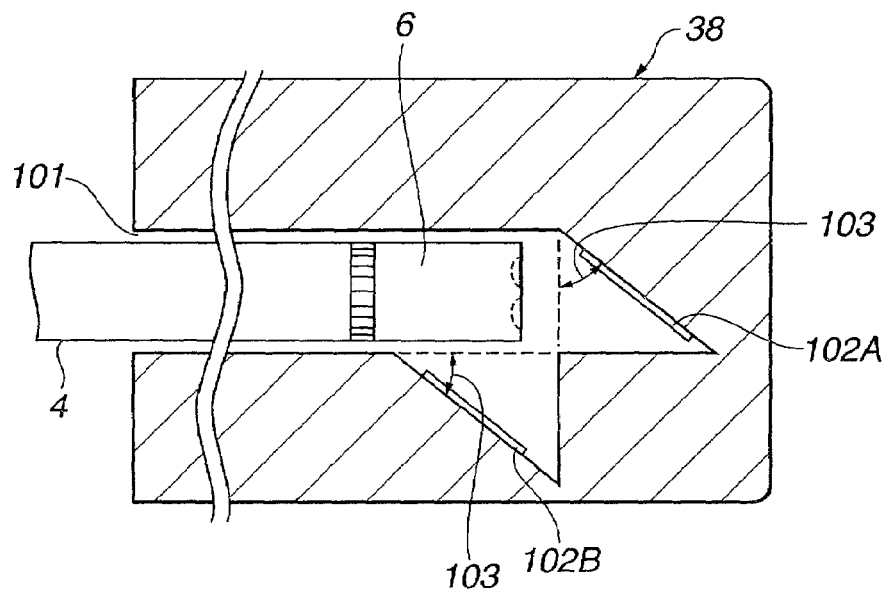
FIG.11C FIG.11D FIG.11E
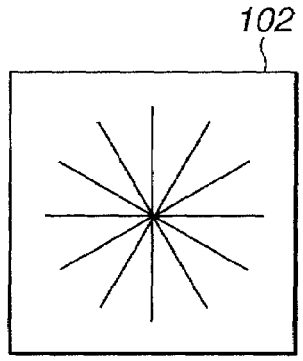 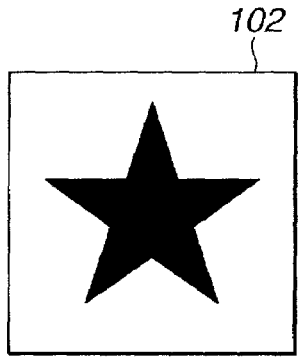 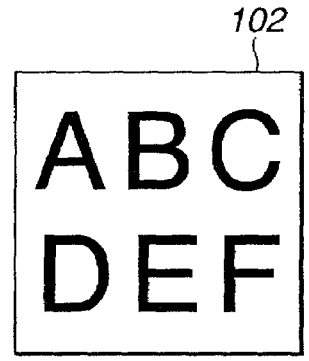

FIG.12A
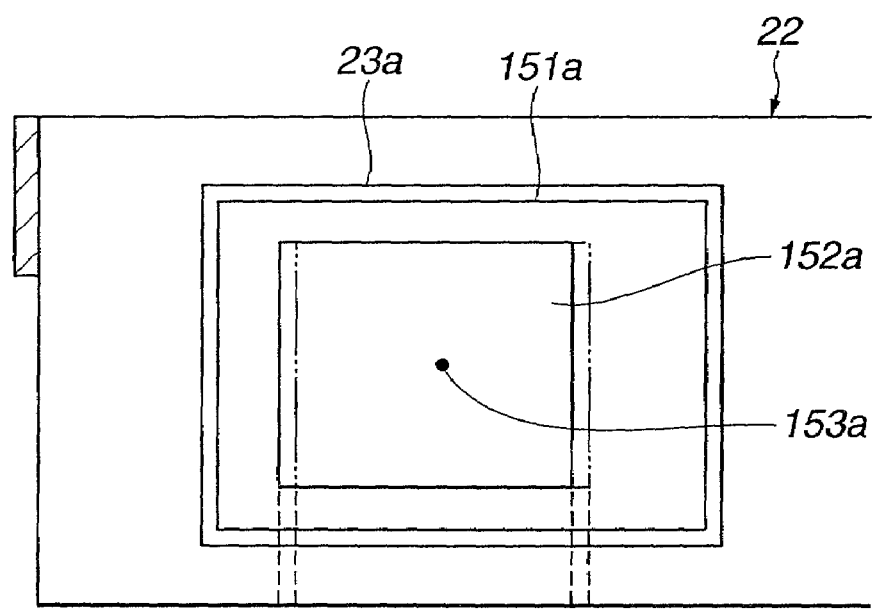
FIG.12B
FIG.12C
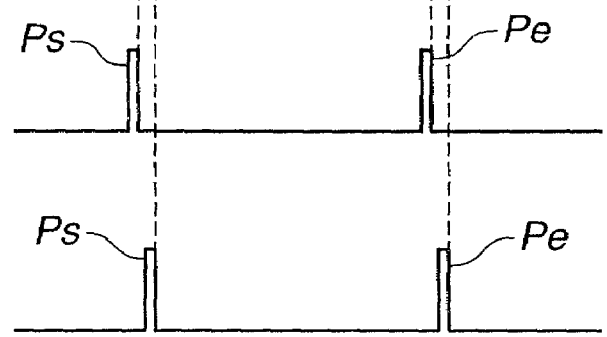

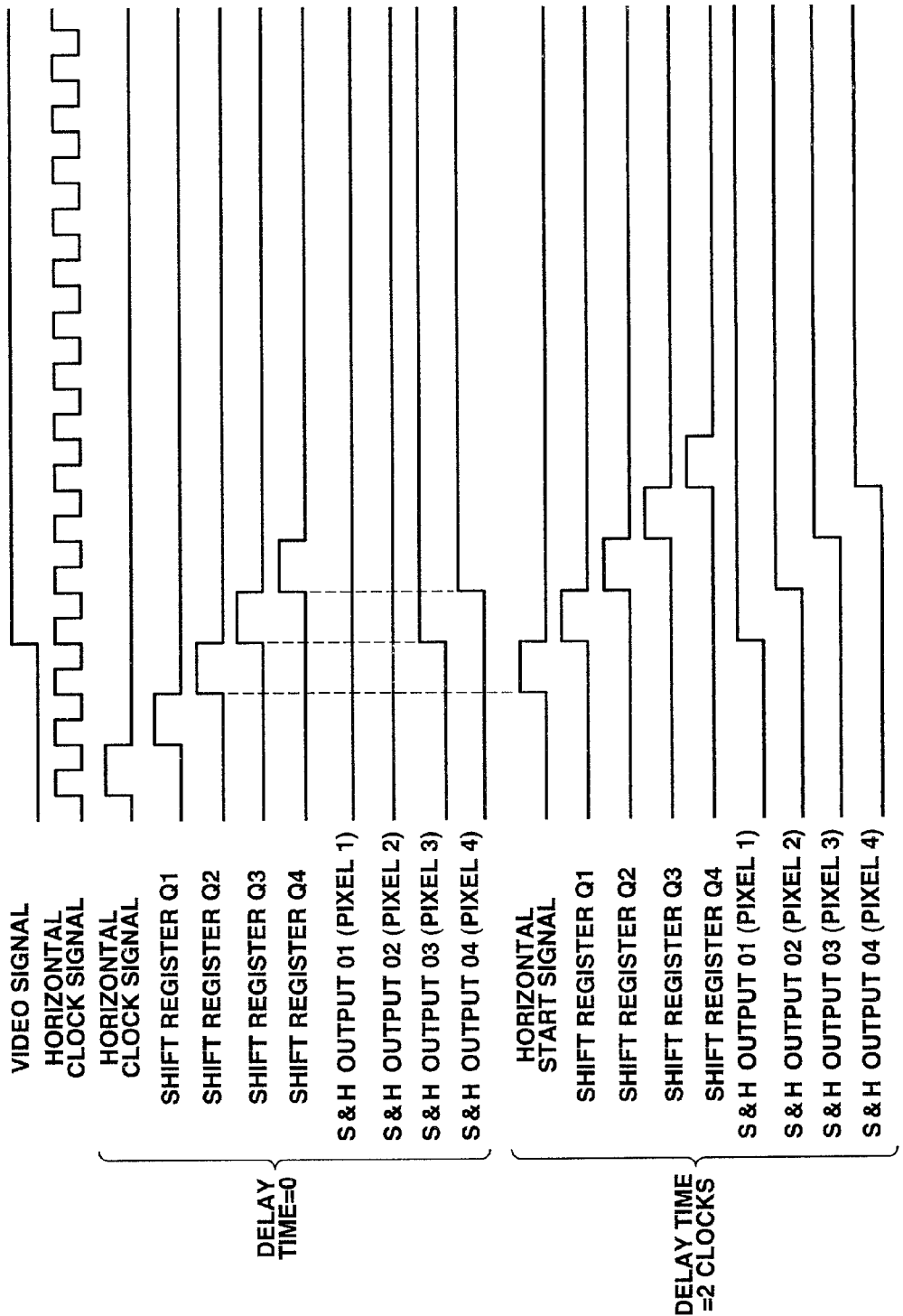

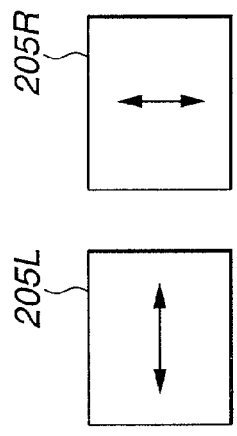
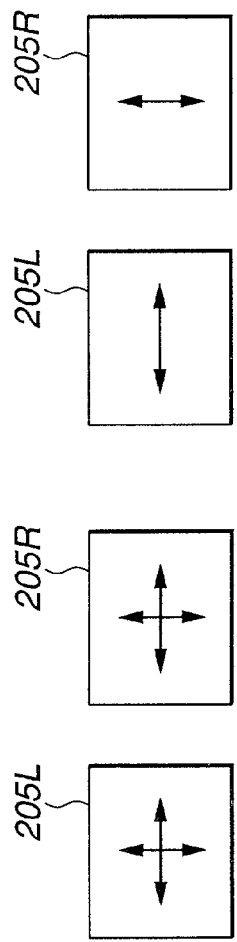
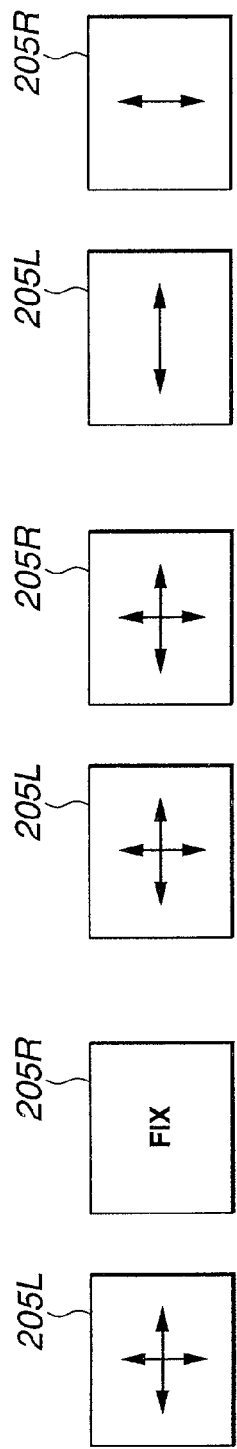
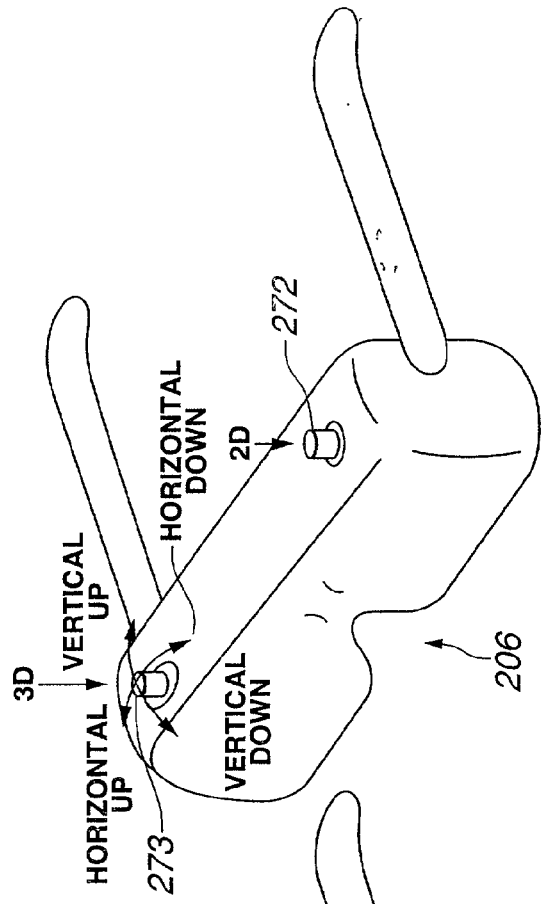
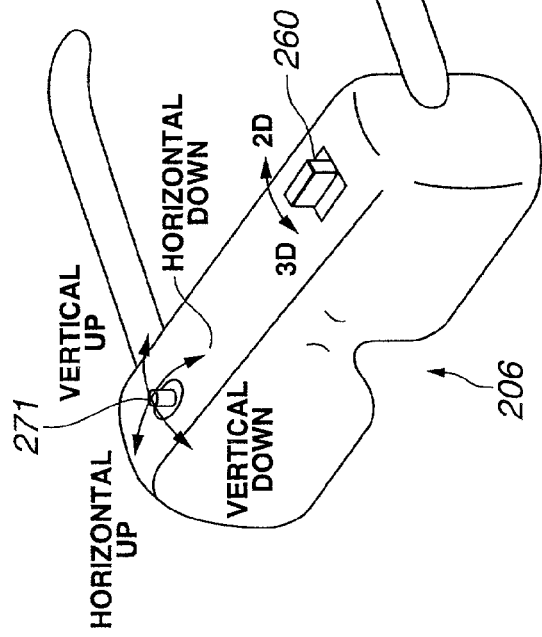

STEREOSCOPIC OBSERVATION SYSTEM

This application claims benefit of Japanese Application Nos. 2001-191556 and 2000-303960 filed on Jun. 25, 2001 and Oct. 3, 2000, the contents of which are incorporated by this reference.

BACKGROUND OF THE INVENTION

1. Field of the Invention

The present invention relates to a stereoscopic observation system having a stereoscopic mode for stereoscopic observation.

U.S. Pat. No. 6,063,023 discloses a related art of a stereoscopic system by attaching an optical adaptor having a stereoscopic optical system to an image pick-up device.

In the related art, the optical adaptor is attached to a main body of a distal tip forming an insertion-portion distal tip, and right and left optical images are formed to the single image pick-up device provided for the main body of the distal tip via left and right objective lenses arranged to the optical adaptor.

In the above-mentioned structure, when the optical adaptor is attached to the main body of the distal tip in an ideal state in which there is neither error nor variation, as shown in FIG. 1A, right and left optical images 132a and 132b are formed onto an image pick-up surface of an image pick-up device 131 at reference positions so that they are, for example, vertically and horizontally symmetric.

However, in general, an error due to the attachment is caused and, consequently, positions of the formed images are vertically shifted, specifically, in the upper direction as shown in FIG. 1B and they are horizontally shifted, specifically, in the left direction as shown in FIG. 1C.

If the positions of the formed images are shifted from the reference position as shown in FIG. 1B or 1C, when the right and left images are displayed on a monitor or the like, right and left images viewed from a user side are shifted from appropriate positions. Thus, when the user observers the images, there is a drawback that burden is applied to user's eye.

If temporary attachment as shown in FIG. 1A, when a face mounted display adaptor (hereinafter, abbreviated to an FMD adaptor) is attached to the face or head of an observer and the right and left images displayed just in front of his eyes are observed, that is, are stereoscopically observed, differences among individuals exist in intervals (parallaxes) between observer's right and left pupils. Therefore, it is preferable to adjust a display position in accordance with the observer who actually uses the FMD adaptor.

SUMMARY OF THE INVENTION

It is one object of the present invention to provide a stereoscopic video image observation system corresponding to the case in which an error is caused by attachment of a stereoscopic optical adaptor and a parallax of an observer is varied.

Further, it is another object of the present invention to provide a stereoscopic video image observation system which enables a stereoscopic video image to be displayed by adjusting a display position corresponding thereto when the error is caused by the attachment of the stereoscopic optical adaptor and the parallax of the observer is varied.

Furthermore, it is another object of the present invention to provide a stereoscopic video image observation system which realizes a stereoscopic function and simultaneously has a display function including a plurality of stereoscopic images for purpose of a high function, small size, and high picture quality.

As the high display-function, a video signal is written to a memory, the written signal is read, and it is sequentially processed in order of fields. Thus, functions of image inversion, Zoom, PinP, etc. are implemented.

According to the present invention, there is provided a stereoscopic video observation system comprising:

an optical adaptor having a stereoscopic optical system;

an image pick-up apparatus to which the optical adaptor is attached, comprising an image pick-up device for forming a stereoscopic image composed of left and right images having a parallax in the left and right directions by the stereoscopic optical system;

a signal processing apparatus for signal processing for processing a signal from the image pick-up device and generating a video signal;

a display control apparatus for controlling a display position of the stereoscopic image in the video signal outputted from the signal processing apparatus; and a display apparatus comprising left and right display devices for changing the display position by the display control apparatus and displaying the left image and the right image just in front of the left and right eyes of an observer.

Thus, when the optical adaptor is attached to the image pick-up apparatus with an error or variation and when there are individual differences of an interval of left and right pupils of the observer, the display control apparatus can adjust the display positions of the left and right images displayed just in front of the left and right eyes of the observer so as to facilitate the stereoscopic observation.

BRIEF DESCRIPTION OF THE DRAWINGS

FIGS. 2 to 12C relate to a first embodiment of the present invention and FIG. 2 is a diagram showing a state in which a video endoscope system is used according to the first embodiment;

FIG. 3 is a cross-sectional view showing the structure when a stereoscopic optical adaptor is attached to a main body of a distal tip;

FIG. 4 is a perspective view showing the resolved structure of an FMD adaptor;

FIGS. 5A to 5C are diagrams showing the structure of an endoscope remote controller and the like;

FIG. 6 is a block diagram showing the structure of an electric system of the FMD adaptor;

FIGS. 7A to 7G are diagrams showing display examples in various display modes;

FIG. 8 is a diagram showing the operation in a 3D mode;

FIG. 9 is a diagram showing the operation of a 3D timer circuit;

FIGS. 10A to 10E are diagrams showing typical operation examples when performing the operation for changing a 2D mode to a 3D mode;

FIGS. 11A to 11E are diagrams showing the structure for correcting a parallax in the 3D mode;

FIGS. 12A to 12C are explanatory diagrams of the operation for adjusting an image display position;

FIGS. 13 to 21B relate to a second embodiment of the present invention, and FIG. 13 is a block diagram showing the structure of a stereoscopic observation system according to the second embodiment;

FIG. 15 is a diagram showing the structure of a liquid crystal display panel;

FIG. 16 is a block diagram showing the detailed structure of an image shift unit;

FIG. 17 is a timing chart showing the comparison between the case in which a delay time of outputs in circuits is zero and the case in which it corresponds to two clocks;

FIGS. 18A to 18C are diagrams showing examples of the schematic structure of delay-amount varying means;

FIGS. 19A and 19B are diagrams showing the appearance of a stereoscopic eye-glass type display apparatus;

FIGS. 20 to 21B relate to a third embodiment of the present invention, and FIG. 20 is a block diagram showing the structure of a stereoscopic observation system according to the third embodiment; and FIGS. 21A and 21B are explanatory diagrams of a function for enlarging an image by an image enlargement processing circuit.

DETAILED DESCRIPTION OF THE PREFERRED EMBODIMENTS

Hereinbelow, embodiments of the present invention will be described with reference to the drawings.

First Embodiment

A first embodiment of the present invention will be described with reference to FIGS. 2 to 12C.

Figure 2:
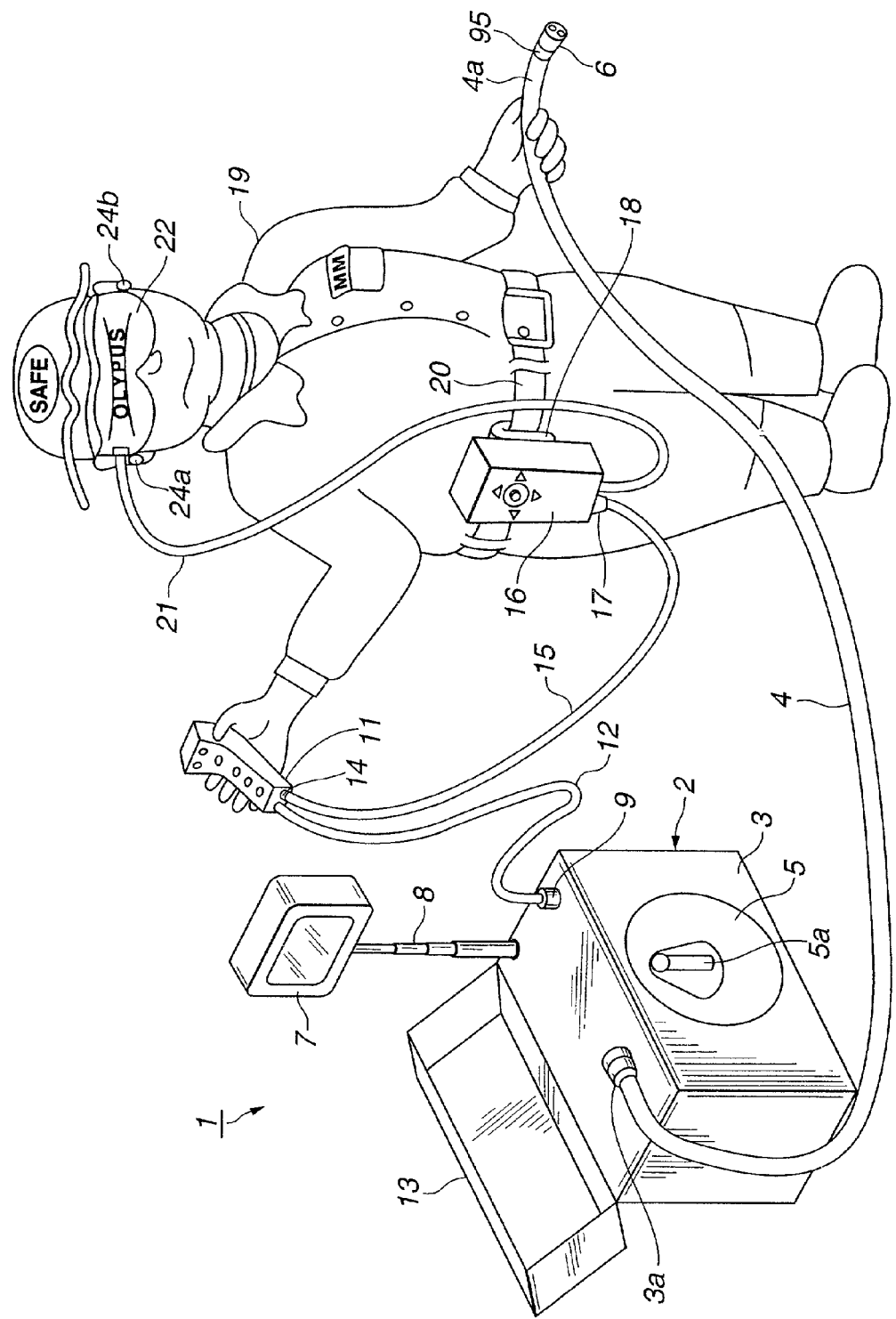

Referring to FIG. 2, in a stereoscopic observation system of the present invention, a video endoscope system 1 according to the first embodiment comprises a box-type video endoscope main body 2. In the video endoscope main body 2, a cylindrical drum (not shown) is accommodated in a box-type case 3. An endoscope insertion portion 4 is wound to the drum. The endoscope insertion portion 4 is pull out from an inlet 3a of an upper surface of the case by rotating the drum. The endoscope insertion portion 4 is accommodated in the case 3 by rotating a handle 5a of a handle cover 5 arranged on a side surface and winding the handle 5a to the drum.

The endoscope insertion portion 4 is flexible. A stereoscopic optical adaptor (stereoscopic optical adaptor) 6 for stereoscopic image pick-up is attached to a distal tip 95 of the endoscope insertion portion 4.

Figure 1A:
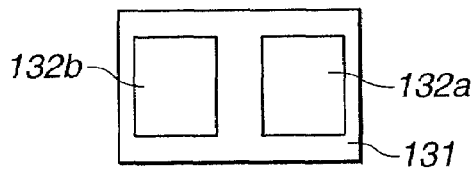
FIGS. 1A to 1C are diagrams showing states for forming images on an image pick-up device.
Figure 1B:
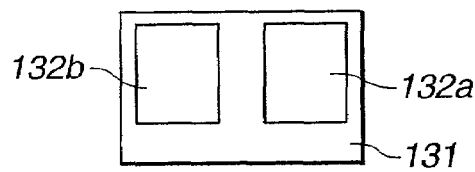
Figure 1C:
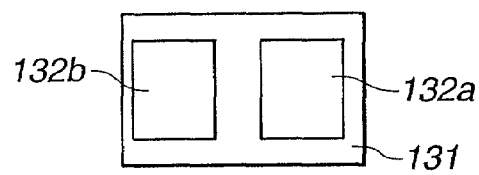
Figure 3:
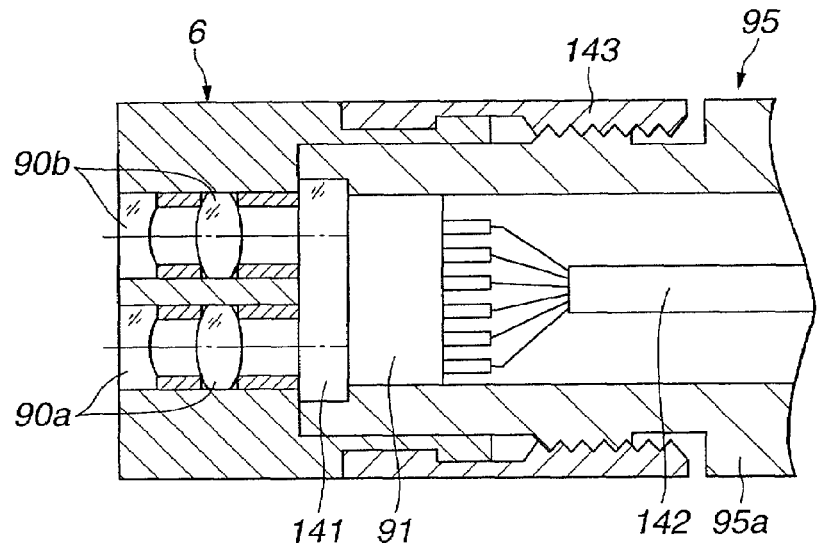

FIG. 3 shows the structure of the distal tip 95 and the stereoscopic optical adaptor 6. As an image pick-up device, a charge-coupled device (hereinafter, abbreviated to a CCD) 91 is attached in the center of a distal tip surface of a distal tip main body 95a forming the distal tip 95. A front surface of the CCD 91 is protected by a cover glass 141. The CCD 91 is connected to one end of a signal cable 142, and another end of the signal cable 142 is connected to a processor 93 (refer to FIG. 8) for signal processing, which is incorporated in the video endoscope main body 2.

The stereoscopic optical adaptor 6 is fit to the distal tip main body 95a. A screw ring 143 arranged to the stereoscopic optical adaptor 6 can be attached (assembled) by being tightened to a screw portion arranged to a circumferential surface of the distal tip main body 95a.

Then, positioning means (not shown) is provided for the distal tip main body 5a and the stereoscopic optical adaptor 6 in the circumferential direction. The positioning operation in the circumferential direction is performed by fitting the stereoscopic optical adaptor 6 to the distal tip main body 95a.

Objective lenses 90a and 90b are attached apart from each other on the left and right to the stereoscopic optical adaptor 6. Left and right optical images having a parallax on the right and left are formed apart from each other on the right and left onto an image pick-up surface of the common CCD 91.

An LCD monitor 7 is arranged elastically by an elastic pole 8 onto the case 3 shown in FIG. 2. The image is displayed on the LCD monitor 7 not in a stereoscopic observation mode for stereoscopic observation (hereinafter, abbreviated to a 3D mode) but in a normal observation mode for observing a normal two-dimensional image (hereinafter, abbreviated to a 2D mode).

A remote controller connector 9 is arranged onto the upper surface of the case 3, and a remote controller cable 12 of an endoscope remote controller 11 is detachably connected. The upper surface of the case 3 can be opened and closed by a cover 13.

An adaptor connector 14 is arranged to the endoscope remote controller 11. One end of an adaptor cable 15 is detachably connected to the adaptor connector 14. Another end of the adaptor cable 15 is detachably connected to an adaptor connector 17 of a face mounted display adaptor (hereinafter, abbreviated to an FMD adaptor) 16.

A belt hook 18 can be attached to the FMD adaptor 16 and is attached to a belt 20 of an observer 19. A goggle cable 21 is pull out from the FMD adaptor 16 and is connected to a stereoscopic FMD goggle (hereinafter, abbreviated to a 3D FMD goggle) 22. A liquid crystal display for the left eye (hereinafter, abbreviated to an L-LCD) 23a and a liquid crystal display for the right eye (hereinafter, abbreviated to an R-LCD) 23b, which display left and right optical images at opposite positions of the left and the right eyes of the observer 19, are arranged to the 3D FMD goggle 22. Goggle ear phones 24a and 24b attachable to the left and right ears are arranged to the 3D FMD goggle 22 (refer to FIG. 6).

Next, the structure of the FMD adaptor 16 will be described with reference to FIG. 4.

The FMD adaptor 16 comprises a top cover 26, a bottom cover 27, a front panel 28, and a plurality of substrates 29 accommodated in them. The belt hook 18 is attached to a rear surface of the bottom cover 27 by a screw or the like.

H1 and H2 position picks 31 for adjusting horizontal positions, V1 and V2 position picks 32 for adjusting vertical positions, an INV switch 33 for inverse display, a Zoom switch 34 for zooming display, a 3D switch 35 for setting the 2D mode to the 3D mode, and a PinP switch 36 for picture-in-picture display are arranged to the front panel 28.

Upon entering the 3D mode, the display mode enters the 3D mode by simultaneously pressing the Zoom switch 34 and the 3D switch 35 or by pressing the 3D switch for two seconds or more. It is devised that the display mode enters the 3D mode only by observer's desired operation.

A picture quality adjustment knob 37 is projected to the upper surface of the top cover 26, thereby changing a picture quality mode such as contrast or the like. The 3D FMD goggle 22 is connected to the FMD adaptor 16 via the goggle cable 21. Further, the adaptor connector 17 is connected to the FMD adaptor 16 and the adaptor cable 15 is also connected.

A parallax adjuster 38 is attached to the front panel 28 of the FMD adaptor 16 and includes calibration marks 102A and 102B for correcting a pupil parallax of the observer himself upon using the 3D mode (refer to FIG. 11A).

The endoscope remote controller 11 will be described with reference to FIGS. 5A to 5C. FIG. 5A shows the structure of the endoscope remote controller 11, FIG. 5B shows a remote controller internal circuit, and FIG. 5C shows a table of a 3D reset signal generating mode.

The remote controller cable 12 and the adaptor cable 15 are connected to the endoscope remote controller 11. Many buttons and joy sticks and the like are provided for the endoscope remote controller 11, thereby intensively executing the operation of the video endoscope main body 2.

The endoscope remote controller 11 comprises a Power button 40 whereby a power source of the video endoscope main body 2 is turned on/off. An index button 41 has a function for thumbnail-displaying a plurality images stored in the video endoscope main body 2.

A menu button 42 is a button which is turned on, thereby displaying a menu screen on a screen. Detailed function settings are called by pressing the menu button 42.

An image processing (instrumentation, etc.) & menu selecting button 43 are 5-Way joy sticks. Instrumentation image processing is executed by pushing the center of the image processing & menu selecting button 43. The displayed menu item can be selected and the function can be selected by the image processing & menu selecting button 43.

Further, although not shown on the image, an on-screen menu for instrumentation is displayed, thereby subsidizing the instrumentation operation.

A center button 44 has a function for return to a neutral position at which a bending operation is not performed. When pressing the center button 44, if the bending operation is performed, the display position is returned to the neutral position at which the bending operation is not performed.

A LIVE button 45 is a button which is pressed, thereby returning the screen to an observation screen without the menu soon even if the menu operation is implemented. An angle joy stick 46 is a joy stick which bends a bending portion 4a near the distal tip of the endoscope insertion portion 4. Upon observation, the angle joy stick 46 is always operated and a view point is moved to a target observation site.

A Zoom button 47 is shifted up (at a position T), thereby linearly enlarging the screen. The Zoom button 47 is shifted down (at a position W), thereby linearly reducing the screen.

A bright button 48 functions for adjusting the brightness of the screen. Each operation for pressing the button leads to a toggle operation by which the brightness of the screen becomes
"dark=>standard=>bright=>standard=>dark=>standard".

A store button 49 executes a function for storing the image to the video endoscope main body 2. A freeze button 50 has a function for forming a still image from the stored image by pressing the button 50.

Next, circuits in the remote controller 11 will be described with reference to FIG. 5B.

The remote controller 11 comprises therein a remote controller CPU 52 for checking states of the various buttons described above in FIG. 5A.

With respect to the remote controller CPU 52, signals of the buttons are connected to I/O ports of the CPU 52 as shown in FIG. 5B. When pressing the buttons, an RS232C (A) circuit 53 transmits an RS232C(A) signal 54 as information to the video endoscope main body 2.

An RS232C(B) circuit 55 transmits an RS232C(B) signal 56 as information to the FMD adaptor 16. Further, a 3D reset signal 57 for forcedly resetting the 3D mode and setting the display mode to the 2D mode can be transmitted to the FMD adaptor 16. FIG. 5C shows conditions for sending the 3D reset signal 57.

The conditions for sending the 3D reset signal 57 are a condition (1) under which the menu button 42 is pressed, a condition (2) under which the index button 41 is pressed, a condition (3) under which the image processing (instrumentation, etc.) & menu selecting button (abbreviated to the image processing instrumentation button in FIG. 5C) 43 is pressed, and a condition (4) under which the Power button 40 is pressed. Under only the four conditions, the 3D reset signal 57 is sent to the FMD adaptor 16. Upon operating other buttons, the 3D reset signal 57 is not generated.

The 3D reset function may be implemented by using the RS232C (B) circuit 55. A signal may be serially transferred via the RS232C(B) circuit 55 under the conditions under which a 3D reset pulse is generated and the 3D mode may forcedly be reset to the 2D mode for the FMD adaptor 16.

Next, the internal structure of the FMD adaptor 16 will be described in detail with reference to FIG. 6.

Referring to FIG. 6, the adaptor connector 17 is connected so that power of 12V is supplied from the endoscope remote controller 11 and it inputs the RS232C(B) signal 56 and the 3D reset signal 57.

The adaptor connector 17 is connected to input a luminance signal (simply abbreviated to a video signal Y) 58 of the video signal from the video endoscope main body 2 and a color signal (abbreviated to a video signal C) 59 of the video signal. The video signal Y58 and the video signal C59 are not L/R field sequential signals but are normal video signals. Further, the adaptor connector 17 is connected to input an Audio signal 60 from the video endoscope main body 2.

The video signal Y58 and the video signal C59 are subjected to color separation processing by a decoder circuit 61, thereby converting them into a Y-signal as a luminance component and an R-Y signal and a B-Y signal as color components (color difference signals). The Y-signal, the R-Y signal, and the B-Y signal are converted into digital video data by an A/D converting circuit 62. The digital video data is inputted to an ODD memory 64 and an EVEN memory 65 as data DataIN 63.

A memory controller 66 performs the control of the operation for writing data and the operation for reading to/from the ODD memory 64 and the EVEN memory 65. The memory controller 66 generates an OW signal 67a as a write control signal of the ODD memory 64, an OR signal 67b as a read control signal of the ODD memory 64, an EW signal 68a as a write control signal of the EVEN memory 65, and an ER signal 68b as a read control signal of the EVEN memory 65.

An FSW 71 controls the switching operation of an O/DataOUT signal 69 read from the ODD memory 64 and an E/Data signal 70 read from the EVEN memory 65 by an FSW signal 72 transmitted from the memory controller 66. The FSW 71 is controlled by using the FSW signal 72, thereby generating an L/R field sequential signal 73.

The DataOUT signals 69 and 70 whose switching is controlled by a switch of the FSW 71 are inputted to a D/A converting circuit 74, and are further converted into the Y signal, the R-Y signal, and the B-Y signal. Moreover, these signals are inputted to an encoder circuit 75, thereby obtaining the L/R field sequential signal 73.

The L/R field sequential signal 73 is transferred to the 3D FMD goggle 22 via the goggle cable 21. The Audio signal 60 connected to the adaptor connector 17 is transmitted via a mute switch 76, and is transferred to the 3D FMD goggle 22 via the goggle cable 21 as an ear phone Audio signal 77.

The switching of the mute switch 76 is controlled by an Audio mute signal 78 transmitted from the memory controller 66. Upon stereoscopically observing the 3D image, the Audio mute signal 78 is valid and the ear phone Audio signal 77 is subjected to mute processing.

A 3D timer circuit 79 for counting time is provided. Upon stereoscopically observing the 3D image, the 3D timer circuit 79 makes a 3D ON signal 80 valid and counts time in the 3D mode. After a predetermined time (e.g., 5 minutes), a 3D OFF signal 81 is transmitted to the memory controller 66, the stereoscopic observation of the 3D image is canceled and the display mode is forcedly shifted to the normal 2D mode. A 3D LED 82 is an LED for flickering upon the stereoscopic observation of the 3D image.

The picture quality adjustment knob 37 transmits a Pic-Cont signal 83 to the memory controller 66, thereby executing a function for adjusting the contrast or color of the image.

Figure 4:
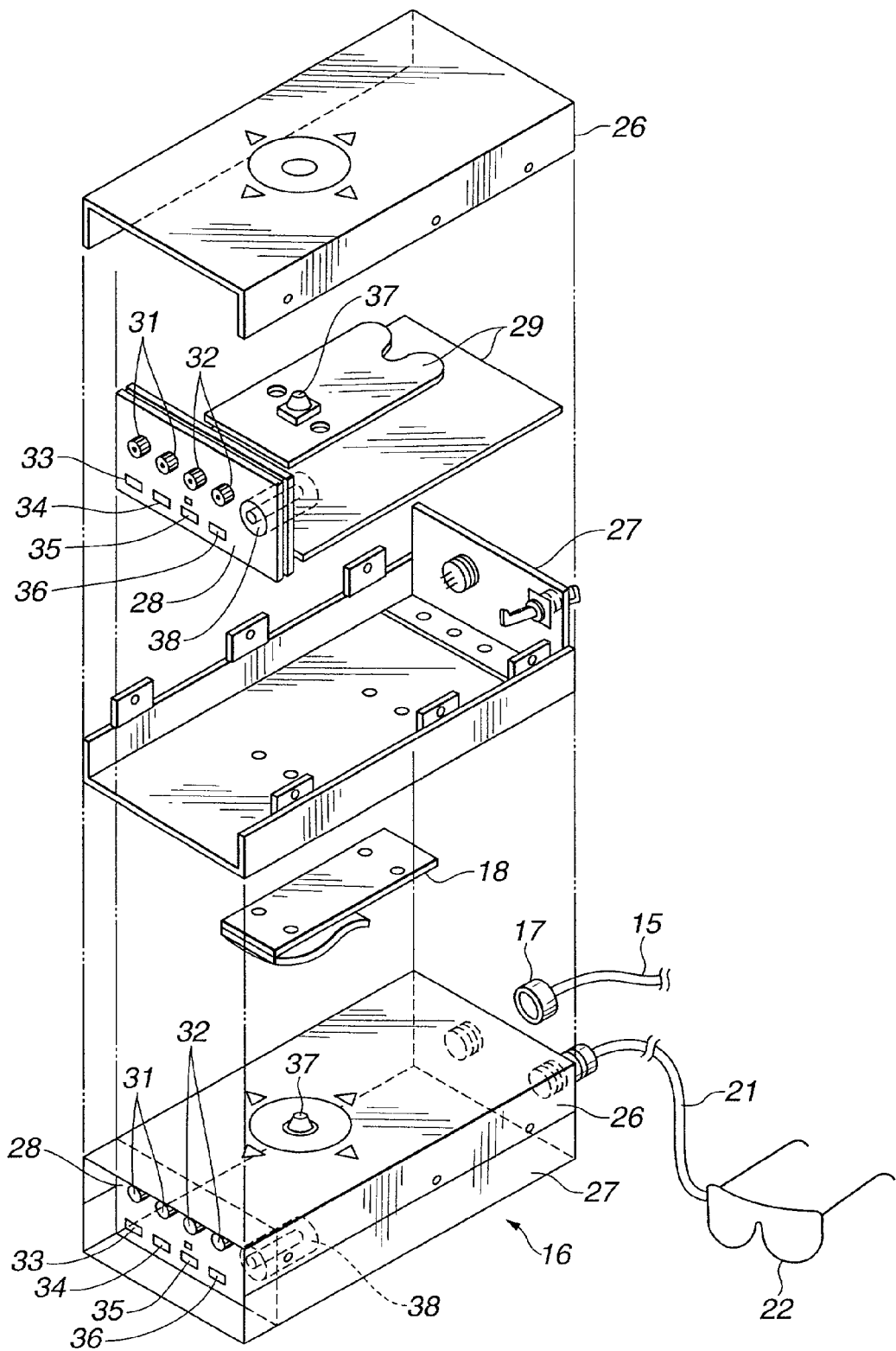

The INV switch 33 connected to the memory controller 66, the Zoom switch 34, the 3D switch 35, the PinP switch 36, the H1 and H2 position picks 31, and the V1 and V2 position picks 32 are the same as those in FIG. 4 described above.

Resistances varied by the H1 and H2 position picks 31 and the V1 and V2 position picks 32 are converted into digital signals via an A/D converter 25 and are inputted to the memory controller 66.

The memory controller 66 receives information of the switches and picks, and controls the operation for reading and writing data to the ODD memory 64 and the EVEN memory 65. The memory controller 66 executes processing in (1) the 2D mode, (2) the Zoom mode, (3) the 3D mode, (4) an INV mode, and (5) a PinP (picture-in-picture) mode and processing for parallel image-shift in the horizontal and vertical directions.

A plurality of picks for adjusting the parallel shift exist among the H1 and H2 position picks 31 and the V1 and V2 position picks 32. In a manual mode, the H1 pick is for coarse adjustment in the horizontal direction, the H2 pick is for fine adjustment in the horizontal direction, the V1 pick is for coarse adjustment in the vertical direction, and the V2 is for fine adjustment in the vertical direction.

Further, in an automatic 3D observation positioning mode, the image is automatically positioned in the horizontal and vertical directions by using the RS232C(A), (B), and (C) based on parallax calibration data upon instrumentation of the stereoscopic image which is held by the endoscope main body 2.

The 3D reset signal 57 is connected to be inputted to the memory controller 66. Upon inputting the 3D reset signal 57, the 3D stereoscopic observation mode is reset and the display mode is forcedly shifted to the 2D normal observation mode.

The RS232C(B) signal 56 is inputted an RS232C(C) circuit 84 and thus becomes the RS232C(C) signal 85 via the RS232C(C) circuit 84. Then, the RS232C(C) signal 85 is inputted to the memory controller 66. The RS232C(C) signal 85 transfers information to the endoscope remote controller 11, mutually transmits information of the key operation of the remote controller 11 and the mode state in the FMD adaptor 16, and the information is transferred under the serial communication control between the remote controller 11 and the FMD adaptor 16.

Hereinbelow, a detailed description is given of the operation of the FMD adaptor 16 described in FIG. 6 with reference to FIGS. 7A to 7G and FIGS. 8 and 9.

FIGS. 7A to 7G are diagrams showing display modes of the FMD. An original image 86 shown in FIG. 7A comprises the video signal Y58 and the video signal C59, as color video signals, transmitted from the video endoscope main body 2.

As the original image 86, examples of the images showing characters A and B are indicated on the left and right. Then, images of the subject formed through the objective lenses 90a and 90b having the parallax become similar. When displaying the menu screen, the images are different on the left and right.

By operating the INV switch 33, the Zoom switch 34, the PinP switch 36, and the 3D switch 35 arranged to the FMD adaptor 16, modes shown in FIGS. 7B to 7G are realized.

When the power source of the FMD adaptor 16 is turned on, the display mode enters the 2D mode shown in FIG. 7B. In the 2D mode, the original image 86 is simultaneously displayed on the L-LCD 23a and the R-LCD 23b of the 3D FMD goggle 22. The 2D mode is a mode in which the normal 2D image is observed by the left and right eyes as it is.

FIG. 7C shows the image in the INV mode. The display mode becomes the INV mode by pressing the INV switch 34. The INV mode is a mode in which vertically inverse (or horizontally reverse) images of the original image 86 are displayed. The inverse images are simultaneously displayed to the L-LCD 23a and the R-LCD 23b of the 3D FMD goggle 22.

FIG. 7D shows the image in the Zoom mode. The display mode becomes the Zoom mode by pressing the Zoom switch 35. In the Zoom mode, only the original image 86 on the left is cut out and is enlarged, and the enlarged image is simultaneously displayed on the L-LCD 23a and the R-LCD 23b of the 3D FMD goggle 22.

FIG. 7E shows the image in the PinP mode. The display mode becomes the PinP mode by pressing the PinP switch 36. In the PinP mode, a real-time moving image 87 and a still image 88 are simultaneously displayed. Incidentally, FIG. 7C shows the vertically inverse images and, however, may show the horizontally reverse images.

In the PinP mode, the real-time moving image 87 is displayed on the still image 88 as a slave screen. Then, the single PinP image is simultaneously displayed on the L-LCD 23a and the R-LCD 23b of the 3D FMD goggle 22.

As means for implementing the 2D mode, the Zoom mode, the INV mode, and the PinP mode, these modes are realized by controlling the operation for writing and reading data to/from the ODD memory 64 and the EVEN memory 65 shown in FIG. 6.

In the 2D mode, the normal 2D mode is obtained by setting a write address and a read address for the ODD memory 64 and the EVEN memory 65 to the same address. Under this control, in the ODD memory 64, the OW signal 67a controls the writing operation and the OR signal 67b controls the reading operation. Similarly, in the EVEN memory 65, the EW signal 68a controls the writing operation and the ER signal 68b controls the reading operation.

In the Zoom mode, in the ODD memory 64 and the EVEN memory 65, an address is set so that the read address is read overlappingly twice in adjacent directions of the horizontal direction and the vertical direction, thereby controlling the operation that a part of the image is zoomed. The OW signal 67a, the OR signal 67b, the EW signal 68a, and the ER signal 68b control the writing and reading operation of the ODD memory 64 and the EVEN memory 65.

In the INV mode, in the ODD memory 64 and the EVEN memory 65, an address is set so that the write address and the read address become vertically inverse (or horizontally inverse) addresses, thereby entering the INV mode. The OW signal 67a, the OR signal 67b, the EW signal 68a, and the ER signal 68b control the writing and reading operation of the ODD memory 64 and the EVEN memory 65.

In the PinP mode, the still image 88 can be displayed by prohibiting the writing processing of the ODD memory 64 and the EVEN memory 65.

Under this control, the OW signal 67a and the EW signal 68a are made invalid, thereby prohibiting the writing processing.

In the PinP mode, only an area for displaying a real-time image is subjected to the writing operation so as to display the real-time image 87. The real-time image can be written to a part of the screen by controlling the write address.

Then, with respect to the reading operation, the normal reading operation may be performed by the OR signal 67b and the ER signal 68b.

Next, FIG. 7F shows the image in the 3D mode. In the 3D mode, the original image on the left is enlarged and displayed on the L-LCD 23a and the original image on the right is enlarged and displayed on the R-LCD 23b.

The 3D mode is one of applications of the Zoom mode. The 3D mode is realized by switching the read addresses of the ODD memory 64 and the EVEN memory 65 in the horizontal and vertical directions by using the ODD memory 64 and the EVEN memory 65 so as to change the address position to be read.

In the 3D mode, in order to correct the variation in values of the pupil parallaxes different depending on the individual observers, there is a function for correcting positions of the right image in the horizontal and vertical directions, relative to the left image. The right image is shifted in the horizontal and vertical directions by correcting the setting of the read address by using the OW signal 67a and the OR signal 67b. FIG. 7G shows the 3D mode without Zooming, and is the same as FIG. 7F, except for no Zooming of the image.

Figure 8:
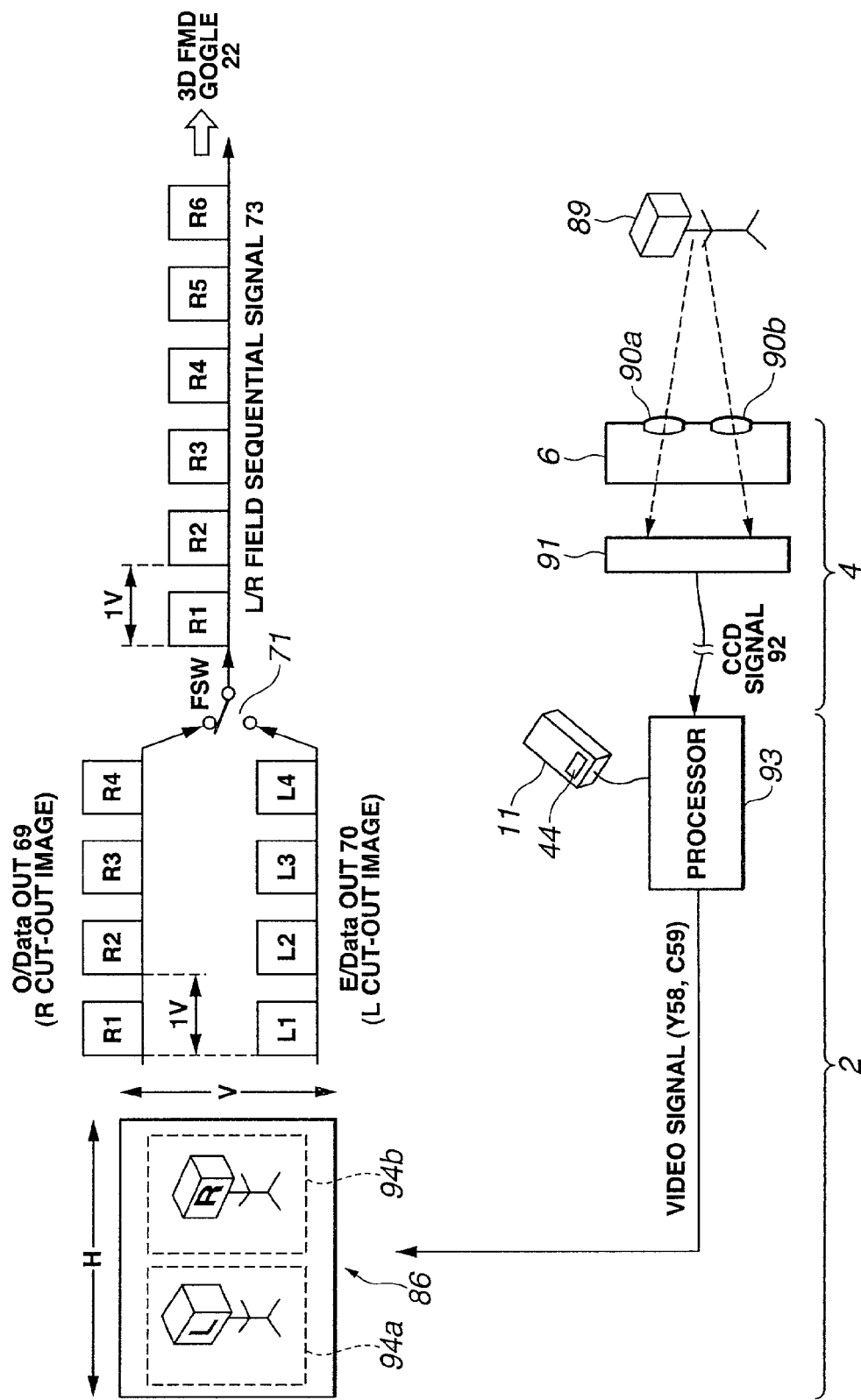

FIG. 8 illustrates the detail of the operation in the 3D mode. Referring to FIG. 8, left and right images (stereoscopic images) of a subject 89 having the parallaxes (of the left and right objective lenses 90a and 90b) are formed at the left and right positions of the single CCD 91 through the left and right objective lenses 90a and 90b arranged to the stereoscopic optical adaptor 6, are photoelectrically converted by the CCD 91, and are picked-up.

A CCD image pick-up signal (abbreviated to a CCD signal) 92 from the CCD 91 is subjected to signal processing by a processor 93 forming a signal processing system of the video endoscope main body 2. The processor 93 in the video endoscope main body 2 outputs the video signal Y58 and the video signal C59 as the video signals. The output signals are displayed, thereby obtaining the original image 86.

The original image 86 is in a normal TV signal format. Two left and right images are formed by the stereo optical adaptor 6 on the original image 86. An L image 94a which is picked up from a left field of view and an R image 94b which is picked up from a right field of view are formed on the single original image 86.

As described in the detailed diagram of the operation of the FMD adaptor 16 in FIG. 6, in the original image 86, the video signal Y58 and the video signal C59 are subjected to the color separation by the decoder circuit 61 and are converted into the Y signal as the luminance component and the R-Y signal and B-Y signals as the color components (color difference signals). The Y signal and the R-Y and B-Y signals are converted into digital video data by the A/D converting circuit 62.

The digital video data is inputted to the ODD memory 64 and the EVEN memory 65 as the DataIN 63. The data is written and read to/from the ODD memory 64. O/DataOUT 69 is data obtained by cutting out only the R image 94b.

The ODD memory 64 outputs serial signals R1 to R4 of only the R image to each field (=1V). Similarly, the data is written and is read to/from the EVEN memory 65. E/DataOUT 70 is data obtained by cutting out only the L image 94a.

The EVEN memory 65 outputs serial signals L1 to L4 of only the L image to each field (=1V).

The O/DataOUT signal 69 read from the ODD memory 64 and the E/DataOUT signal 70 read from the EVEN memory 65 are switch-controlled by the FSW signal 72 transmitted from the memory controller 66 by using the switch FSW 71. The L/R field sequential signal 73 is generated by controlling the FSW 71 using the FSW signal 72 (further, via the D/A converting circuit 74 and the encoder circuit 75).

As described in the operation of FIG. 6, the L/R field sequential signal 73 is received by the 3D FMD goggle 22, the R image 94b is sequentially displayed to the R-LCD 23b every field, and the L image 94a is displayed to the L-LCD 23a.

The pair of L image and R image having the parallax is observed by a pair of left and right LCDs (L-LCD 23a and R-LCD 23b) of the 3D FMD goggle 22. Therefore, the observer 19 using the 3D FMD goggle 22 can confirm the stereoscopic observation image.

Figure 9:
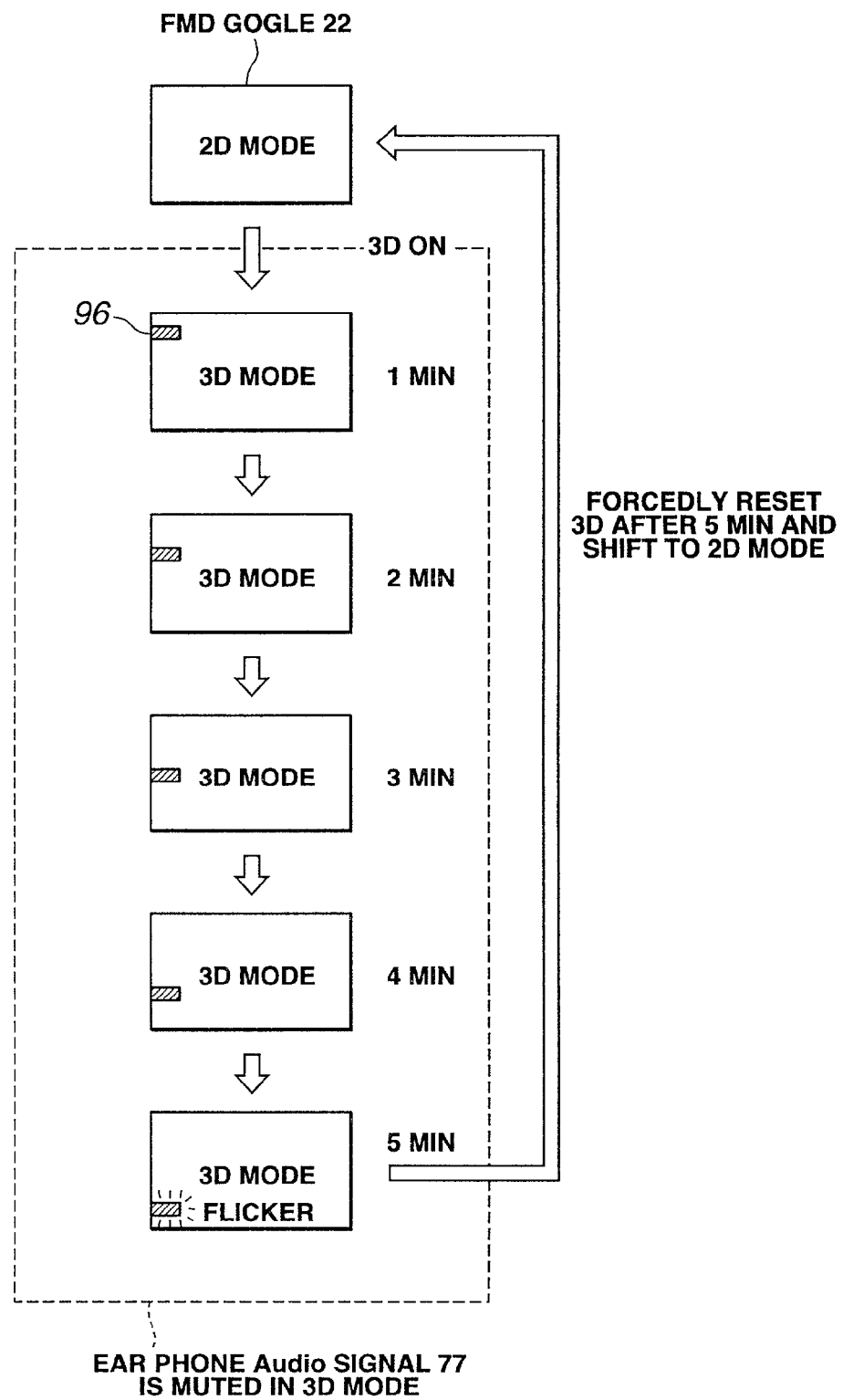

Further, the operation of the 3D timer circuit 79 will be described with reference to FIG. 9.

Upon stereoscopically observing the 3D image, the 3D ON signal 80 is made valid and, then, the 3D timer circuit 79 shown in FIG. 6 counts time in the 3D mode. Referring to FIG. 9, the 3D timer circuit 79 counts time starting from on-time of the 3D mode at which the 2D mode shifts to the 3D mode. An indicator 96 is displayed on the screen of the 3D FMD goggle 22.

In the indicator 96, the display position is horizontally changed every minute in accordance with a pass time from the start of the 3D mode. A display example of five minutes of the 3D timer is shown in FIG. 9. After five minutes, the indicator 96 starts to flicker. When the flickering ends, the 3D mode is canceled because five minutes pass.

Incidentally, in the 3D mode shown by surrounding of a broken line, sound is vanished so that the observer can concentrate to the stereoscopic observation by muting the ear phone Audio signal 77. Then, the display operation of the 3D timer circuit 79 is not limited to the displaying operation of the indicator 96 shown in FIG. 9. For example, the display operation can be performed by indicating the time pass by using numbers, by changing the color, by changing the brightness of the indicator, or the like.

With the system shown in FIG. 8, the operation upon observing the image of the video endoscope main body 2 using the 3D FMD goggle 22 will be described in detail with reference to FIGS. 10A to 10E.

FIG. 10A shows the original image 86. The original image 86 is displayed in the 2D mode in a state in which the menu button 44 is pressed. A menu display 97 is overlaid and is displayed on the original image 86.

Menus such as "title/image/display image/record/SETUP/initialize" are displayed on the menu display 97. In this case, upon using the stereoscopic optical adaptor 6, the menu display 97 is overlaid and is displayed on the left picked-up image of the L image 94*a*, as shown in FIG. 10A.

Upon switching on the 3D mode switch 35 in this state, the right image is appropriately displayed to a right eye 98*b* corresponding to the R-LCD 23*b* on the 3D FMD goggle 22, as shown in FIG. 10C. On the other hand, as shown in FIG. 10B, the image obtained by overlaying the menu is viewed to a left eye 98*a* corresponding to the L-LCD 23*a* without change.

When the image processing (instrumentation, etc.) & menu selecting button 43 for menu operation is operated in the states shown in FIGS. 10B and 10C and the menu is shifted to "title==>image", the menu is selected and the 3D reset signal 57 is generated. FIGS. 10D and 10E show a state in which the 3D reset signal 57 is generated.

The 3D mode is canceled and is forcedly shifted to the 2D mode by generating the 3D reset signal 57. In this case, the menu operation is easy because the same 2D image can be viewed by the left eye 98*a* and the right eye 98*b*.

In the 3D mode described with reference to FIGS. 10A to 10E, the control of the indication and operation of the menu display has such a specification that the 3D reset signal 57 is generated by operating the image processing & menu selecting button 43. However, the 3D reset signal 57 may be generated just after the menu operation in the 3D mode.

According to the first embodiment, when overlaying on-screen graphic information (character information) which does not need the stereoscopic display operation in the 3D mode for stereoscopic observation, means for generating the reset signal so as to reset the 3D mode and display the image in the 2D mode is provided. Therefore, it is easily solved that the lack of the on-screen graphics on one of the left and right screens is caused and on-screen graphic character information is overlaid and is hardly displayed (depending on the correction of observer's pupil parallax).

Upon displaying a thumbnail image by operating the index button 41, the 3D reset signal 57 is generated and the 3D mode is changed to the 2D mode.

As shown in FIG. 5C, when the Power button 40 is operated, the 3D reset signal is generated and the display operation is initialized in the 2D mode.

Next, a description is given of means for correcting the parallax of the individual (observer) in the 3D mode, that is, for controlling the display positions of the L image and the R image on the L-LCD 23*a* and the R-LCD 23*b* with reference to FIGS. 11A to 11E. Incidentally, if there is an error due to the attachment of the stereoscopic optical adaptor 6 to the distal tip main body 95*a*, it will be understood that the control of the display positions become valid based on the following description.

That is, upon correcting the parallax by the individual, the parallax adjuster 38 shown in FIG. 11A is used. As shown in FIG. 11B, upon using the parallax adjuster 38, the endoscope insertion portion 4 to which the stereoscopic optical adaptor 6 is attached is inserted to an adjuster hole 101. The calibration mark 102A or 102B is observed in the 3D mode depending on the stereoscopic optical adaptor 6 for direct sight or for indirect sight.

That is, the calibration mark 102A for direct sight and the calibration mark 102B for indirect sight are arranged in the adjuster hole 101.

FIGS. 11C to 11E show examples of the calibration marks 102 (in the present specification, reference numeral 102 typically denotes 102A and 102B). FIG. 11C shows the mark of a linear pattern, FIG. 11D shows a figure pattern, and FIG. 11E shows an example of a character pattern.

According to a method for correcting the individual parallax, the display mode enters the 3D mode. Then, when observing the calibration mark 102 by the 3D FMD goggle 22, the 3D FMD goggle 22 is adjusted depending on the individuals so as to recognize the calibration mark 102 on the left and right eyes without offset.

The adjusting method is realized by adjusting the H1 and H2 position picks 31 and the V1 and V2 position picks 32 arranged to the front panel 28. The one-time setting of the H1 and H2 position picks 31 and the V1 and V2 position picks 32 is held if the power is turned off.

FIGS. 12A to 12C show the operation for adjusting the display positions by adjusting the H1 and H2 position picks 31.

When the observer 19 observes the image in the 3D mode through the 3D FMD goggle 22, it is assumed that the center position of the L image 152*a* is shifted to the left from a reference position 153*a* which is easily observed opposite to the left pupil position and is displayed on a display screen 151*a* of the L-LCD 23*a* just in front of the left eye. FIG. 12A shows this state.

The display mode is shifted to a display position adjusting mode by operating a display position adjustment switch (not shown) in this state and, further, the display position of the L image 152*a* is set to be in an adjustable state.

In this state, by operating the H1 and H2 position picks 31 to change a variable resistance, the memory controller 66 in FIG. 6 shifts the position of the read address of data of the L image 152*a* from the EVEN memory 65, to the horizontal direction.

When the variable resistance is set to the center within a variable range and is increased from the set center resistance, a start address for starting the reading operation in the horizontal direction is increased. The display position of the L image 152*a* can be moved to the left. On the contrary, when the resistance is decreased, the start address for starting the reading operation in the horizontal direction is decreased and the display start position of the L image 152*a* can be moved to the right.

Consequently, when it is assumed that reference symbol Ps denotes a start pulse for starting the display to start the reading operation in the horizontal direction in FIG. 12B showing that the L image 152*a* is displayed in FIG. 12A, the adjustment of the resistance to have a small level causes the start pulse Ps for starting the display to start the reading operation in the horizontal direction to be shifted to the right, thereby shifting the L image 152*a* to the right, as shown by a broken line in FIG. 12C. The display position can be variably set to an appropriate position at which the observer 19 can easily observe the image. Incidentally, referring to FIGS. 12B and 12C, reference symbol Pe denotes a pulse for ending the display operation.

Herein, the adjustment in the horizontal direction is described. However, the display position can be adjusted in the vertical direction. Further, the adjustment of the L image 152*a* is described herein. However, the R image can similarly be adjusted independently.

The calibration mark 102 is arranged, neither in the vertical nor in the parallel direction of the stereoscopic optical adaptor 6, but with an angle of a predetermined angle 103 as shown in FIG. 11B. The display position can be adjusted in a state in which the parallax from the stereoscopic optical adaptor 6 is maximum and the calibration mark 102 can easily be adjusted.

According to the first embodiment, when the on-screen graphics such as the menu are multiplexed and are displayed in the observation state of the 3D mode, the 3D mode is reset and canceled and is forcedly shifted to the 2D mode. Therefore, it is possible to easily observe the screen in the same display state by the left and right eyes without overlaying the on-screen indication and the causing the lack of the indication.

As a consequence, in the menu screen, it is possible to realize an environment under which the screens of the same display contents are checked by the left and right eyes and desired selection can easily be performed.

Further, according to the first embodiment, when the left and right pupil positions of the observer are different depending on the individuals, the display operation can be executed in easy observation because the display positions of the left and right images can be adjusted in the horizontal and vertical direction.

Furthermore, according to the first embodiment, when the stereoscopic optical adaptor 6 is attached to the distal tip main body 95a with the error and variation, the display position can be adjusted in accordance with the pupil positions of the observer who actually observes the stereoscopic image. Therefore, it is possible to cope with the variation in working precision of the stereoscopic optical adaptor 6 or the distal tip main body 95a. The manufacturing costs of the endoscope insertion portion 4 can be decreased.

According to the first embodiment, a description is given of the case in which the stereoscopic optical adaptor 6 is attached to the CCD 91 mounted on the distal tip main body 95a as the image pick-up apparatus for capturing the stereoscopic image. However, it will obviously be understood that it is possible to also apply to the present invention, an image pick-up apparatus dedicated for the stereoscopic observation in which the stereoscopic optical adaptor 6 is integrally fixed to the distal tip main body 95a, for example, a video endoscope dedicated for stereoscopic observation.

Second Embodiment

Next, a second embodiment of the present invention will be described with reference to FIGS. 13 to 19B.

A stereoscopic observation system 201 shown in FIG. 13 comprises an image pick-up apparatus for pick up of a stereoscopic image (hereinafter, abbreviated to an image pick-up apparatus) 202, a camera control unit (abbreviated to a CCU) 203 for video signal generation processing based on an image pick-up signal outputted from the image pick-up apparatus 202, and a Face Mount Display (abbreviated to an FMD) 206 forming a stereoscopic eye-glass type display device for displaying left and right video images (images) to left and right liquid crystal display panels 205L and 205R by inputting a video signal 204 outputted from the CCU 203.

The image pick-up apparatus 202 comprises left and right objective lenses 207L and 207R having the same optical characteristics, and a single image pick-up device 209 comprising charge-coupled devices arranged to the image forming positions of the objective lenses 207L and 207R so as to pick up the images of a subject 208 through the two objective lenses 207L and 207R.

Figure 14A:
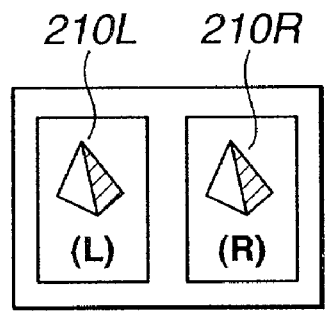
FIGS. 14A to 14E are explanatory diagrams of image shift by right and left image shift circuits.

The two objective lenses 207L and 207R are deviated and arranged to the left and right from the center position of the image pick-up device 209. Left and right images 210L and 210R having the parallax to the subject 208 are separated to the left and right on the image pick up device, as shown in FIG. 14A and are formed.

The image pick-up signal photoelectrically converted by the image pick-up device 209 is inputted to the CCU 203 and it is subjected to the video signal generation processing by the CCU 203. A standard video signal 204 such as an NTSC signal or a PAL signal is generated. The video signal 204 is outputted to the FMD 206 from a video output terminal.

The video signal 204 is inputted to an RGB decoder 211 in the FMD 206. The RGB decoder 211 separates the video signal 204 into a video signal component and a synchronous signal component, specifically, RGB signals R, G, and B and a synchronous signal SYNC. The RGB signals R, G, and B are inputted to video signal input terminals of the left and right liquid crystal display panels 205L and 205R, specifically, R, G, and B input terminals.

The synchronous signal SYNC is inputted to a timing generator 216.

The timing generator 216 drives the left and right liquid crystal display panels 205L and 205R, and outputs a horizontal start signal 217 and a vertical start signal 218 for determining the display positions of the image to left and right image shift circuits 219 and 220. Further, the left and right image shift circuits 219 and 220 apply to a horizontal start signal input terminal (abbreviated to an H start in FIG. 13 or the like) and a vertical start signal input terminal (abbreviated to a V start in FIG. 13 or the like), horizontal start signals 221 and 222 and vertical start signals 223 and 224 which are generated by delaying the horizontal start signal 217 and the vertical start signal 218 to be inputted.

In this case, the horizontal start signal 217 and the vertical start signal 218 generated by the timing generator 216 are applied to the left and right liquid crystal panels 205L and 205R, not via the left and right image shift circuits 219 and 220. Then, images formed on the image pick-up surface of the image pick-up device 209, namely, images of the video signals 204 without change corresponding to the images 210L and 210R in FIG. 14A are displayed to the liquid crystal display panels 205L and 205R. For the sake of a brief description, the images 210L and 210R are used as left and right images displayed on the liquid crystal panels 205L and 205R.

Figures 14B, 14D:
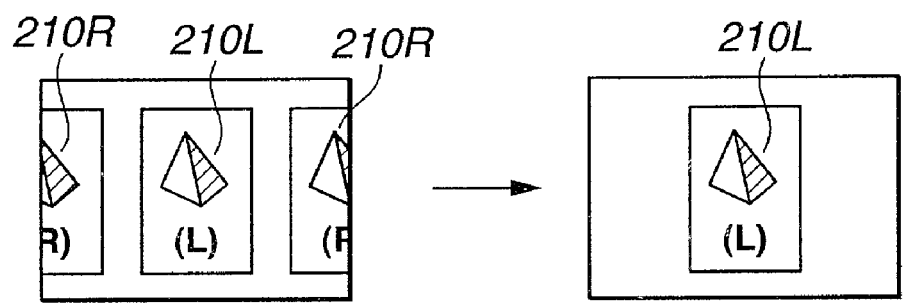
Figures 14C, 14E:
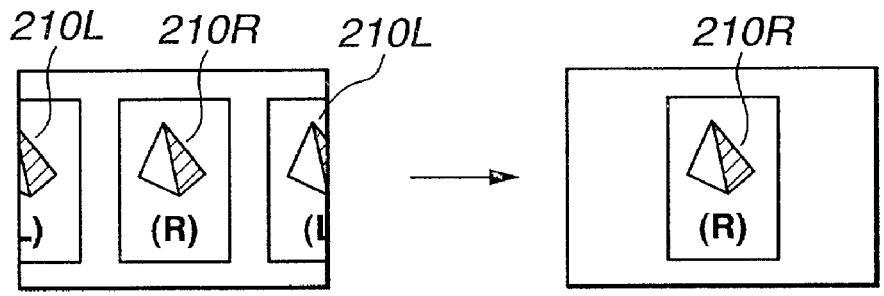

The image shift circuits 219 and 220 form display position setting means which performs signal processing (more specifically, display control or signal delay processing of a display drive signal) for shifting the images in the horizontal and vertical directions so that the images 210L and 210R displayed in FIG. 14A are displayed to areas in the center of the display surfaces of the left and right liquid crystal display panels 205L and 205R as shown in FIGS. 14B and 14C.

The horizontal start signal 217 and the vertical start signal 218 from the timing generator 216 are set to the horizontal start signals 221 and 222 and the vertical start signals 223 and 224 which are subjected to processing for shifting and displaying the image of the image shift circuits 219 and 220. The horizontal start signals 221 and 222 and the vertical start signals 223 and 224 are applied to the left and right liquid crystal display panel 205L and 205R.

Only in the processing for shifting the images of the image shift circuits 219 and 220, the images 210L and 210R in FIG. 14A correspond to the images 210L and 210R, as observation targets, which are shifted in the center as shown in FIGS. 14B and 14C. Other images 210L and 210R are divided into half on both sides and are displayed. Thus, these images disturb the observation.

Mask plates (for shielding light at the left and right corners excluding the center area) are arranged to the left and right liquid crystal display panels 205L and 205R so that only other images 210L and 210R as the observation targets are displayed at the areas in the center. Or, a masking circuit (not shown) is provided between the RGB decoder 211 and the left and right liquid crystal panels 205L and 205R so that an image portion which is electrically unnecessary is masked. When the user actually observes the left and right liquid crystal panels 205L and 205R by the left and right eyes, only the images 210L and 210R are observed as the observation targets, as shown in FIGS. 14D and 14E.

Figure 15:
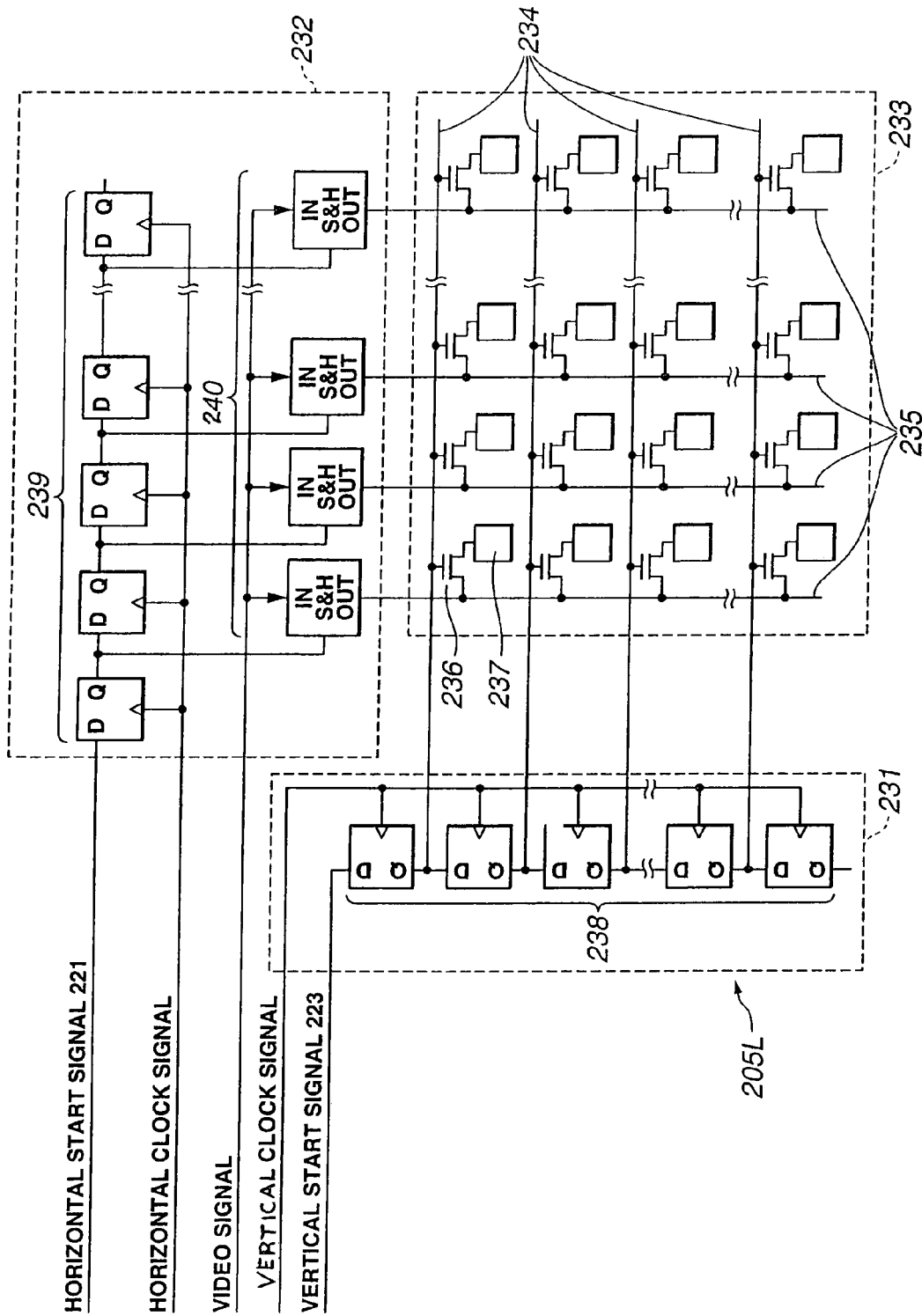

FIG. 15 shows the structure of the active-matrix-driving-system liquid crystal display panel 205L (similar in the case of 205R) arranged in the FMD 206.

The liquid crystal display panel 205L mainly comprises an address portion 231, a data portion 232, and a display portion 233. The address portion 231 selects an address bus line corresponding to one line of an address bus 234 of the display portion 233 by sequentially scanning the lines, and the data portion 232 supplies the video signal (RGB signal) corresponding to each line of the display portion 233 to a data bus 235.

The display portion 233 is enclosed by sandwiching liquid crystal to two plain glass substrates. A transparent electrode is arranged over one glass substrate and is connected to a predetermined potential.

A large number of address buses 234 and the data bus 235 run latticelike in the horizontal and vertical directions via an insulating film on the other glass substrate. A field electric transistor (abbreviated to an FET) 236 is arranged at each intersection of the address buses 234 and the data buses 235. A gate of each FET 236 is connected to the address bus 234 and a drain is connected to the data bus 235.

A source of each FET 236 is connected to many transparent electrodes 237 arranged like mosaics. A liquid crystal display portion corresponding to one pixel is formed of one transparent electrode 237, the liquid crystal adjacent thereto, and other transparent electrodes (over the glass substrate).

Each pixel is assumed as a capacitor of a parallel plain electrode. When a specific address line is set to be in a "High" state, the FET 236 connected to the address bus line is turned on, electric signals from the data bus 235 flow to the FET 236 corresponding to one line in a lump.

On the other hand, since all the FETs 236 connected to the address bus line in a "Low" state are off, the capacitors connected thereto are not disturbed by signals of the data buses 235. Then, stored charges are continuously held. A two-dimensional optical image is obtained by using change characteristics in optical nature of the liquid crystal due to the electric field by the charges stored in the capacitor.

The address portion 231 comprises a shift register 238 using a large number of flip-flops. The vertical start signal 223, which is "High" at time intervals of one vertical clock is supplied to an input terminal D (of a first-step flip-flop) of the shift register 238. An output Q of each flip-flop is connected to the address bus line. A vertical clock signal is applied to a clock input terminal of each flip-flop.

The vertical start signal 223 is transferred synchronously with the vertical clock signal, thereby sequentially transferring the "High" address signal to a lower line of the address bus 234.

On the other hand, the data portion 232 comprises a shift register 239 for receiving the horizontal start signal 221 and sampling and holding circuits 240 for receiving signals of the outputs Q of many flip-flops forming the shift register 239 and sampling and holding the signals (a sampling and holding circuit forming the sampling and holding circuits 240 in FIG. 15, etc. is abbreviated to an S and H).

A horizontal clock signal is applied to a clock input terminal of each flip-flop of the shift register 239. The "High" horizontal start signal 223 is applied to an input terminal D (of a first-step flip-flop) of the shift register 239 at the time interval of one horizontal clock.

The video signals are inputted to input terminals of the sampling and holding circuits 240. Output terminals of the sampling and holding circuits 240 are connected to data bus lines.

Referring to FIG. 17, the horizontal start signals are sequentially transferred one by one in the horizontal direction by the shift register 239 synchronously with the horizontal clock signal. The sampling and holding circuit connected to the output terminal which holds the horizontal start signal samples the video signal.

Before and after inputting the horizontal start signal, the sampling and holding circuit holds the video signal.

FIG. 17 shows a timing chart for indicating that the display position of the image is changed by delaying the horizontal start signal upon the zero delay time for delaying no horizontal start signal to the upper direction and upon the delay time corresponding to two clocks of the horizontal start signal to the lower direction.

Upon the zero delay time for delaying no horizontal start signal, an output O3 of the sampling and holding circuit (at a third step from the first step) is first set to "High" indicating "bright" (outputs O1 and O2 of the sampling and holding circuits at the first and second steps are set to "Low" indicating "dark"). On the other hand, upon the delay time corresponding to the two clocks, the output O1 of the sampling and holding circuit at the first step is first set to "High". That is, the sampling and holding operation is performed earlier by the two clocks and, in other words, this means that the display position is shifted to the left on the display screen (by a time of the two clocks). Therefore, the image shift means delays the start signal, thereby realizing a function for shifting the image.

Figure 13:
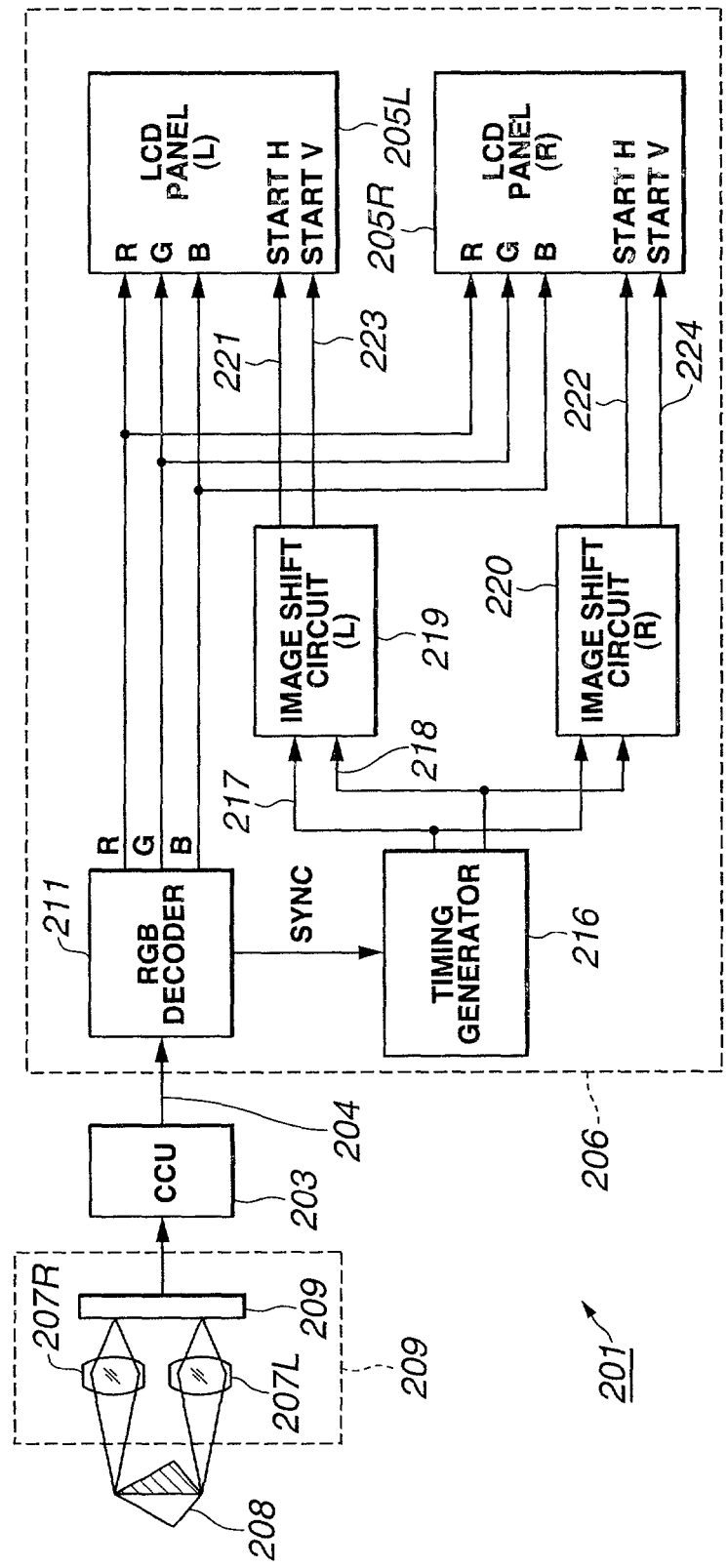
Figure 16:
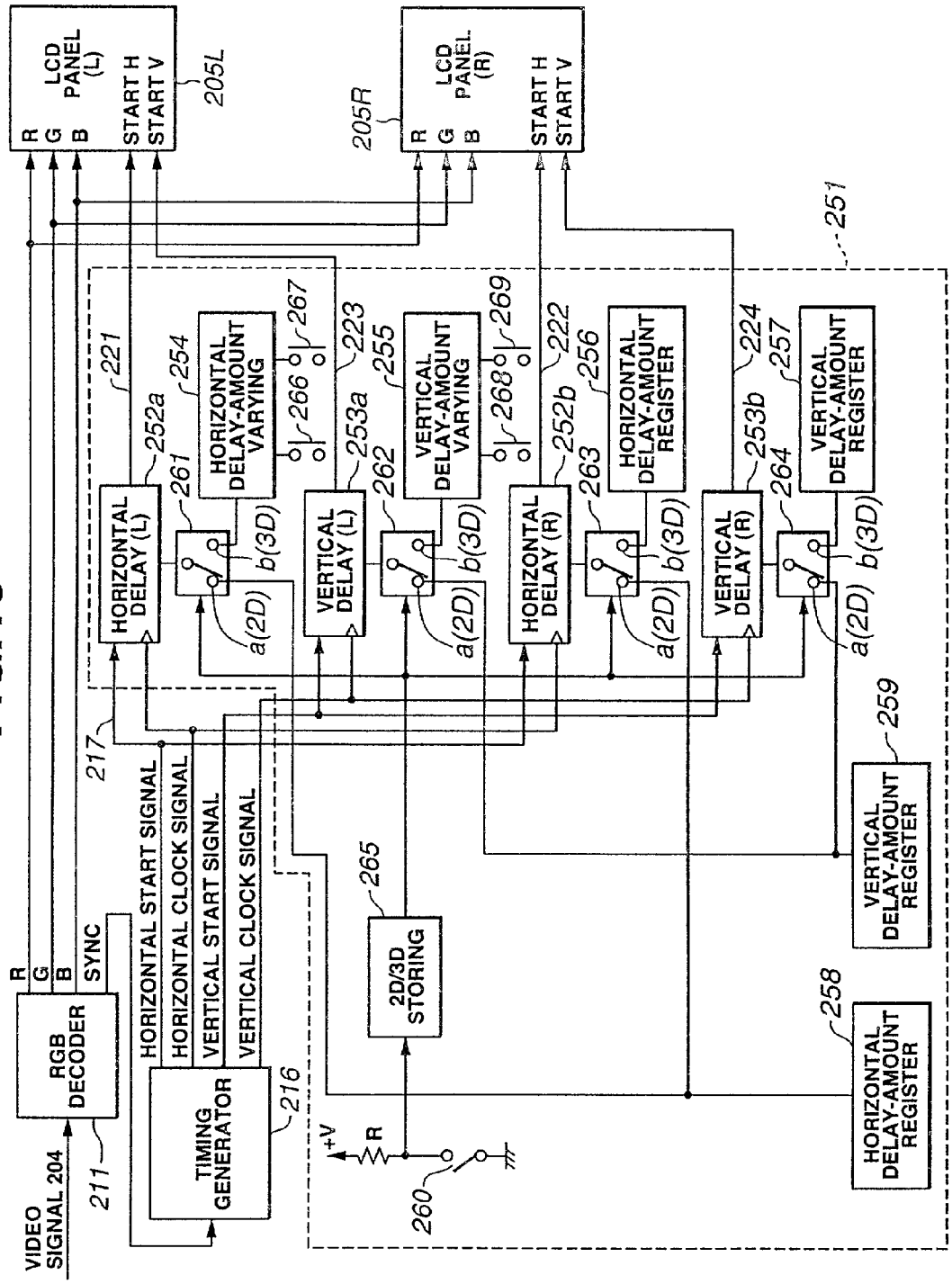

FIG. 16 shows a block diagram showing in detail the structure of the image shift circuits 219 and 220 in FIG. 13, namely, of an image shift unit 251 for delaying the horizontal start signal 217 and the vertical start signal 218.

The image shift unit 251 comprises: left and right horizontal delay circuits 252a and 252b for receiving the horizontal start signal 217 and the horizontal clock signal from the timing generator 216; left and right vertical delay circuits 253a and 253b for receiving the vertical start signal 218 and the vertical clock signal from the timing generator 216; a horizontal delay-amount variably setting circuit 254 and a vertical delay-amount variably setting circuit 255 for variably setting the amount of delay in the case of stereoscopically displaying the image (abbreviated to the 3D display or 3D) of one of the left and right horizontal delay circuits 252a and 252b and of one of the left and right vertical delay circuits 253a and 253b (herein, the horizontal delay circuit 252a and the vertical delay circuit 253a); a horizontal delay-amount register 256 and a vertical delay-amount register 257 for setting the amount of delay in the 3D display of the other horizontal delay circuit 252b and the vertical delay circuit 253b; a horizontal delay-amount register 258 and a vertical delay-amount register 259 for setting the amount of delay in the case of normal display (that is, abbreviated to the 2D display or 2D for commonly displaying the one image having no parallax on the left and right) without the 3D display of the left and right horizontal delay circuits 252a and 252b and the left and right vertical delay circuits 253a and 253b; a 2D/3D selecting switch 260 for selecting the 2D/3D display; and a 2D/3D setting storing circuit 265 for storing a mode to be displayed and controlling the switching of the change-over switches 261 to 264 for connecting a selection signal in a predetermined mode upon turning on the power to input terminals for setting the amount of delay of the left and right horizontal delay circuits 252a and 252b and the left and right vertical delay circuits 253a and 253b.

The left and right horizontal delay circuits 252a and 252b and the left and right vertical delay circuits 253a and 253b comprise a data loadable down counter (data presettable counter). The horizontal delay-amount varying circuit 254 and the vertical delay-amount varying circuit 255 comprise an up/down counter. The horizontal delay-amount can variably be set by an up switch 266 and a down switch 267. The vertical delay-amount can variably be set by an up switch 268 and a down switch 269.

The change-over switches 261 to 264 connected to the left and right horizontal delay circuits 252a and 252b and the left and right vertical delay circuits 253a and 253b are switched interlockingly with the 2D side of a contact a and the 3D side of a contact b via the 2D/3D setting storing circuit 265 by the operation of the 2D/3D selecting switch 260. Upon turning on the power, the setting is performed by an output signal from the 2D/3D setting storing circuit 265 so as to select a preset mode.

According to the second embodiment, the stereoscopic observation system comprises:

a first display panel and a second display panel having an input unit of a display control signal (display drive signal) for determining the display position of the image of video signals, in which a subject image is picked up to a first area and a second area of the image pick-up device 209 by using the left and right objective lenses 207L and 207R and the video signals generated from the output signals are inputted to first and second video input terminals; and display position setting means for supplying the display control signal, by which pixels of the image of the video signals correspond to display pixels of the first and second display panels, to the input unit of the display control signal of the first and second display panels so that the subject image formed to the first area of an image pick-up surface of the image pick-up device 209 is displayed as an image at a predetermined position of the first display panel from among the subject images formed on the image pick-up surface and the subject image formed on the second area of the image pick-up surface is displayed as an image at a predetermined position of the second display panel.

According to the second embodiment, as mentioned above, the video signal is not subjected to the signal processing (image processing) but the control signal for controlling the image display is subjected to the delay processing, thus to generate the corrected control signal. Consequently, the image display position of the common video signal in the left and right image display means is shifted and the image display suitable to the stereoscopic observation is set. Further, the stereoscopic observation can be performed with inexpensive circuit parts.

Next, a specific description is given of the shift in the horizontal direction in the operation principle of the image shift unit 251 in FIG. 16. The shift in the vertical direction can fundamentally be described with the same principle.

The horizontal start signal 221 which is set to the "High" at the time interval of one horizontal clock outputted from the timing generator 216 is applied to a data load terminal of the data loadable down-counter forming the horizontal delay circuit 252a. Then, data on the amount of delay applied to the data terminal is used as a count start value. In this case, the data on the amount of delay applied to the data terminal has different values depending on the 2D/3D modes.

Moreover, values in the 3D mode are different depending on the left eye and the right eye. In the 2D mode, the same image needs to be displayed in the center for the left eye and the right eye. Therefore, the same amount of delay is added to the values for the left eye and the right eye. The amount of delay in this case is set to values by which any of the image 210L for the left eye and the image 210R for the right eye is displayed in the center, by the horizontal delay-amount register 258.

On the other hand, in the 3D mode, the delay amount in the horizontal direction of the horizontal delay-amount varying register 254 is set so that the image 210L for the left eye is displayed in the center of the liquid crystal display panel 205L for the left eye in the left and right directions, and the delay amount in the horizontal direction of the horizontal delay-amount register 256 is set so that the image 210R for the right eye is displayed in the center of the liquid crystal display panel 205R for the right eye in the left and right directions.

When setting the data on the amount of delay to the data loadable down counter, the count-down operation starts from the next horizontal clock signal. As a counting result, the data becomes zero, the "High" signal at the time interval corresponding to the length one horizontal clock is outputted to the liquid crystal display panel 205L as the horizontal start signal 221. Therefore, as larger the loaded data is, the delay time is long and the image is shifted to the left.

By slightly delaying the image 210R for the right eye in FIG. 14A in the horizontal direction, the image 210R for the right eye is set to be displayed in the center area of the display screen. However, the image 210L for the left eye has already been located on the left of the center area in the horizontal direction and, therefore, the image 210L for the left eye can be set to be displayed in the center area in the horizontal direction with the shift of one line in the vertical direction by delaying the image 210L for the left eye further in the horizontal direction than the display operation at the left end of the display screen in this case.

This time (in the second embodiment), the down counter is used. However, the above-mentioned result is obtained by detecting the zero delay time by using the up counter and outputting the "High" signal as the horizontal start signal 221 to the liquid crystal display panel 205L at the time interval of the length corresponding to one clock. Then, as larger the loaded data is, in this case, the delay time becomes shorter.

The user (observer) can select and set the display mode from the 2D mode to the 3D one or, on the contrary, freely can select and set the display mode by operating the 2D/3D selecting switch 260. If the display mode is stored by the 2D/3D setting storing circuit 265, the desired display mode can be set upon turning on the power. Incidentally, upon turning on the power, in many cases, the user can easily use the system by generally setting the display mode to the 2D mode.

According to the second embodiment, the horizontal delay-amount variably setting circuit 254 and the vertical delay-amount variably setting circuit 255 for setting the amount of delay in the 3D mode of the horizontal delay circuit 252a and the vertical delay circuit 253a for the left eye are formed by the up/down counter. The operator can change the count value of the (preset) data by which the amount of delay in the horizontal direction (or in the vertical direction) is determined, by pressing the up switch 266 (or 268) or the down switch 267 (or 269).

Incidentally, the amount of delay in the 3D mode of the horizontal delay circuit 252b for the right eye and the vertical delay circuit 253b for the right eye is set by the horizontal delay-amount register 256 and the vertical delay-amount register 257. On the other hand, as mentioned above, the amount of delay in the 3D mode of the horizontal delay circuit 252a for the left eye and the vertical delay circuit 253a for the left eye can freely be set variably.

As mentioned above, the purpose for setting any of the delay means to the delay-amount varying means is to adjust the pupil distance in the horizontal direction having individual differences depending on the observer and to adjust an inclination of the image in the vertical direction, which is caused by the error due to the attachment of the image pick-up device or the objective lens.

Preferably, a delay-time limiting circuit (not shown) may be provided to limit a varying range of the delay time of the up/down counter in some degree.

Although the delay-amount varying means may be provided for the left and right eyes, respectively, the delay-amount varying means may be used for the one eye and a fixed value may be used for the other eye, as mentioned above. The amount of delay may be varied for the one eye only in the horizontal direction and it may be varied for the other eye only in the vertical direction.

FIGS. 18A to 18C show the above-mentioned states. FIG. 18A corresponds to the case of the image shift unit 251 shown in FIG. 16. FIG. 18B corresponds to the case in which the amount of delay in the 3D mode by the horizontal delay circuit 252b and the vertical delay circuit 253b in FIG. 16 is varied by the delay-amount varying means composed of the up/down counter in place of the horizontal delay-amount register 256 and the vertical delay-amount register 257.

FIG. 18C corresponds to the case in which the vertical delay-amount varying circuit 255 and the vertical delay-amount register 257 in FIG. 16 are exchanged.

The 2D/3D selecting switch 260, the up switches 266 and 268 for varying the amount of the delay, and the down switches 267 and 269 have, for example, the arrangement shown in FIG. 19A. However, they may have the arrangement shown in FIG. 19B.

Referring to FIG. 19A, by horizontally operating the 2D/3D selecting switch 260 arranged near the upper left position of the FMD 206, the 3D mode and 2D mode can be switched (selected). When a joy stick (or acute point) 271 is provided near the upper right and when the joy stick 271 is vertically operated, the amount of the delay in the vertical direction can be down or up. When the joy stick 271 is horizontally operated, the amount of delay in the horizontal direction can be down or up.

Referring to FIG. 19B, a button switch 272 for the 2D mode, and a joy stick 273 shared with the function of the button switch for the 3D mode are provided. By pressing the button switch 272 for the 2D mode, the 2D mode is selected. By pressing the joy stick 273, the 3D mode is selected. A function for vertically or horizontally operating the joy stick 273 is the same as the case of the joy stick 271 in FIG. 19A.

The second embodiment has the following advantages.

That is, the display position of the image is changed by the delay circuit comprising the counter and, therefore, the circuit structure can be inexpensive, light, and small-sized.

The left and right images are dedicatedly displayed on the left and right display panels. Thus, advantageously, the image can stereoscopically be observed without flickering and the burden to the eyes is reduced.

In the related art in which the image of the display means arranged in front thereof is observed by the eye glasses using a liquid crystal shutter so as to stereoscopically observe the image, the unnecessary video image due to the reflection of ambient light is observed on the display means and the image cannot be viewed. However, according to the second embodiment, since the eye glasses for displaying the left and right images just in front of the left and right eyes are used, the image can easily be observed without the influence of the ambient light.

Third Embodiment

Next, a third embodiment of the present invention will be described with reference to FIGS. 20 to 21B.

Figure 20:
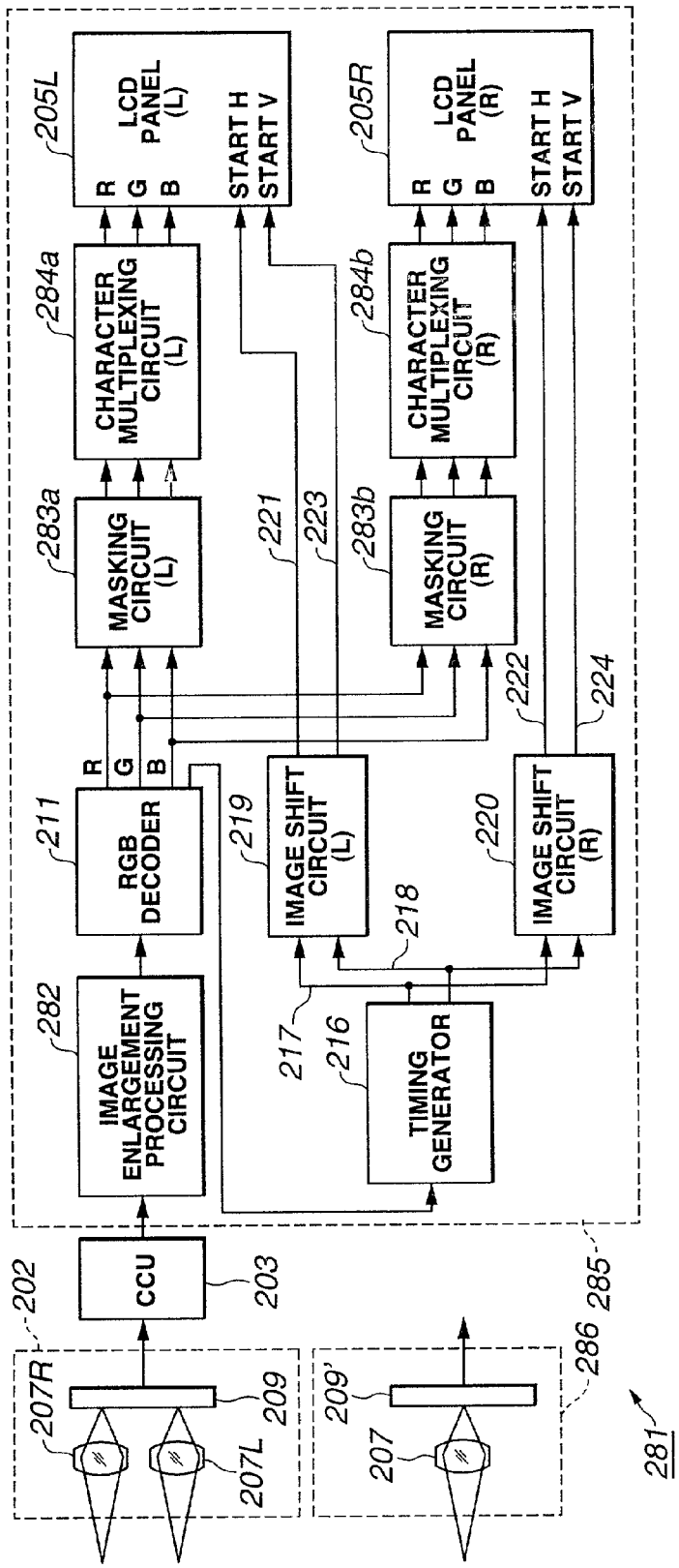

According to the third embodiment, a stereoscopic observation system 281 shown in FIG. 20 is formed in such a manner that an image enlargement processing circuit 282 for image enlargement processing is inserted between the CCU 203 and the RGB decoder 211 in the stereoscopic observation system 201 in FIG. 13 and an FMD 285 is used with the structure in which masking circuits 283a and 283b for masking processing and character multiplexing circuits 284a and 284b for multiplexing the character signal (to the video signal) are inserted between the R, G, and B video signal input terminals of the RGB decoder 211 and the R, G, and B video signal input terminals of the left and right liquid crystal display panels 205L and 205R.

Further, according to the third embodiment, in addition to the stereoscopic image pick-up apparatus (3D image pickup apparatus) 202, a 2D image pick-up apparatus 286 comprising a single objective lens 207 and an image pick-up device 209' is connected to the CCU 203 and is used.

As described according to the second embodiment, the masking circuits 283a and 283b perform the masking processing in which the video signal is displayed only in the center of the image and other portions are replaced with a black image in the 3D mode when the pair of the objective lenses 207L and 207R is arranged in front of the image pickup device 209 and the left and right images are formed at the different positions.

Further, it is possible to prohibit the masking processing so that the 2D image pick-up apparatus 286 is used, the single objective lens 207 is arranged in front of the image pick-up device 209', the image is formed over the image pick-up surface and, then, the obtained image (without lack) can be displayed on the full screen.

Masking reset switches (not shown) are connected to the masking circuits 283a and 283b. When the masking reset switches are not operated, the unnecessary image is masked as described according to the second embodiment. When the masking reset switches are operated, the masking processing is prohibited.

The character multiplexing circuits 284a and 284b are provided. The character in the display mode (e.g., the 2D or 3D character) is displayed on the liquid crystal display panels 205L and 205R based on the 2D/3D display mode selected by the observer by the character multiplexing circuits 284a and 284b. Thus, the observer can promptly know the current display mode.

Figure 21A:
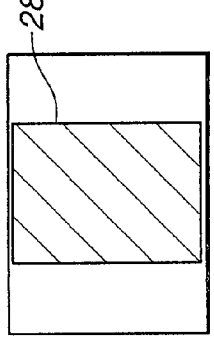
Figure 21B:
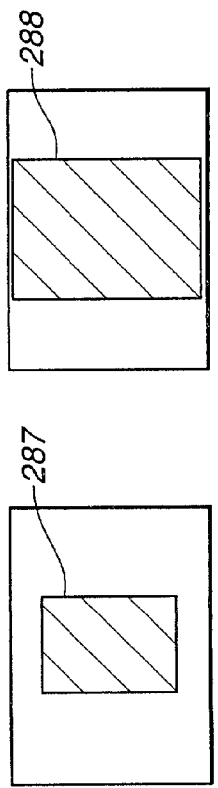

The image enlargement processing circuit 282 is provided between the CCU 203 and the RGB decoder 211, thereby enlarging the image 287 shown in FIG. 21A in a manner as shown in FIG. 21B and obtaining a large image 288. Accordingly, the 3D image can further easily be observed. Also, the 2D image can easily be observed.

Others are the same as those according to the second embodiment. According to the third embodiment, the observer can easily know whether the image which is actually observed is the image in the 2D mode or the image in the 3D mode based on the character in the display mode.

The image enlargement processing circuit 282 is provided. As a consequence, the enlarged image is obtained and the 3D image can further easily be observed. The use of the 2D image pick-up apparatus 286 enables the observation without narrowing the display range of the observation image in this case. Additionally, the same advantages according to the second embodiment are obtained.

As will obviously be understood, in the stereoscopic observation system according to the second and third embodiments, the display position of the image is changed by the delay circuit comprising the counter. Therefore, the circuits can be inexpensive, light, and small-sized. As compared with a stereoscopic observation system with eye glasses using a liquid crystal shutter, the image can stereoscopically be observed without flickering. Consequently, the burden to the eyes is reduced.

Incidentally, an embodiment in which the above embodiments are partly combined belongs to the present invention.

Also, having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A stereoscopic video observation system comprising:
    an optical adaptor having a stereoscopic optical system;
    an image pick-up apparatus to which said optical adaptor is attached, comprising an image pick-up device for forming a stereoscopic image composed of left and right images having a parallax in the left and right directions by said stereoscopic optical system;
    a signal processing apparatus for signal processing for processing a signal from said image pick-up device and generating a video signal;
    a display control apparatus for controlling a display position of said stereoscopic image in the video signal outputted from said signal processing apparatus said display position being dictated by a position of an observer's left and right eyes;
    a display apparatus comprising left and right display devices for changing the display position by said display control apparatus so that said left image and said right image are positioned and displayed just in front of and aligned with said observer's left and right eyes;
    wherein said display control apparatus controlling a display start signal of said left and right display devices of said display apparatus, and supplying a display control signal, corresponding to display pixels of said left and right display devices, for forming said stereoscopic image in said video signal of said left and right display devices, thereby controlling the display positions of said left and right images displayed on said left and right display devices, said display control signal being a two-valued digital signal.

2. A stereoscopic video observation system according to claim 1, wherein said display apparatus is detachably attached near the head or the face of the observer, and is a face mounted display comprising said left and right display devices for displaying said left and right images just in front of the left and right eyes of the observer.

3. A stereoscopic video observation system according to claim 1, wherein said display control apparatus A/D converts a video signal including said stereoscopic image outputted from said signal processing apparatus, records the A/D converted signal to a memory, and thereafter controls the display position by operating a read memory address.

4. A stereoscopic video observation system according to claim 1, wherein the video signals of the left and right images for forming said stereoscopic image are sequentially inputted to said display apparatus in order of fields.

5. A stereoscopic video observation system according to claim 1, wherein as means for correcting a parallax upon stereoscopic observation or an error due to the attachment of said optical adaptor, any of a linear pattern, a figure pattern, and a character pattern is used as a calibration mark.

6. A stereoscopic video observation system according to claim 1, wherein said image pick-up apparatus having said image pick-up device is a video endoscope having an insertion portion which is inserted into a subject.

7. A stereoscopic video observation system according to claim 2, wherein said display control apparatus or said face mounted display is portable for an observer.

8. A stereoscopic video observation system according to claim 2, wherein when transferring sound to said face mounted display, the sound can be muted upon stereoscopic observation.

9. A stereoscopic video observation system according to claim 1, wherein a stereoscopic observation time or the remaining stereoscopic observation time is displayed to said display apparatus upon stereoscopic observation.

10. A stereoscopic video observation system according to claim 1, wherein said display control apparatus can switch any of an image inverse mode, a Zoom mode, a PinP (picture in picture) mode, and a stereoscopic observation mode.

11. A stereoscopic video observation system according to claim 1, wherein said display control apparatus can correct an error of an image forming position of the stereoscopic image onto said image pick-up device, which is caused upon attaching said optical adaptor.

12. A stereoscopic video observation system according to claim 1, wherein said display control apparatus can independently adjust the display positions of said left and right images displayed on said left and right display devices.

13. A stereoscopic video observation system comprising:
    an image pick-up apparatus having an image pick-up device for forming a stereoscopic image composed of left and right images having a parallax in left and right directions by a stereoscopic optical system;
    a signal processing apparatus for signal processing for processing a signal from said image pick-up device and generating a video signal;
    a display control apparatus for controlling a display position of said stereoscopic image in the video signal outputted from said signal processing apparatus said display position being dictated by a position of an observer's left and right eyes;
    a display apparatus comprising left and right display devices for changing the display position by said display control apparatus so that said stereoscopic image is positioned and displayed just in front of and aligned with said observer's left and right eyes;
    wherein said display control apparatus controlling a display start signal of said left and right display devices of said display apparatus, and supplying a display control signal, corresponding to display pixels of said left and right display devices, for forming said stereoscopic image in said video signal of said left and right display devices, thereby controlling the display positions of said left and right images displayed on said left and right display devices, said display control signal being a two-valued digital signal.

14. A stereoscopic video observation system according to claim 13, wherein said display apparatus is detachably attached near the head or the face of the observer, and is a face mounted display comprising said left and right display devices for displaying said left and right images just in front of the left and right eyes of the observer.

15. A stereoscopic video observation system according to claim 13, wherein the video signals of the left and right images for forming said stereoscopic image are sequentially inputted to said display apparatus in order of fields.

16. A stereoscopic video observation system according to claim 13, further comprising correction means for correcting a parallax upon stereoscopic observation or an error due to the attachment of a stereoscopic optical adaptor, said correction means employing any of a linear pattern, a figure pattern, and a character pattern as a calibration mark.

17. A stereoscopic video observation system according to claim 13, wherein said image pick-up apparatus comprising said image pick-up device is a video endoscope having an insertion portion which is inserted in a subject.

* * * * *